(12) United States Patent
Huang et al.

(10) Patent No.: US 7,728,036 B2
(45) Date of Patent: Jun. 1, 2010

(54) METHODS FOR DELIVERY OF CATECHOLIC BUTANES FOR TREATMENT OF TUMORS

(75) Inventors: Ru Chih C. Huang, Baltimore, MD (US); Richard Park, Baltimore, MD (US); Chih-Chuan Chang, Baltimore, MD (US); Yu-Chuan Liang, Baltimore, MD (US); David Mold, Baltimore, MD (US); Elaine Lin, New York, NY (US); Jonathan Heller, Raleigh, NC (US); Neil Frazer, Cary, NC (US)

(73) Assignees: Erimos Pharmaceuticals, LLC, Houston, TX (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/284,111

(22) Filed: Nov. 21, 2005

(65) Prior Publication Data

US 2006/0141025 A1 Jun. 29, 2006

Related U.S. Application Data

(63) Continuation of application No. PCT/US2004/016235, filed on May 20, 2004.

(60) Provisional application No. 60/472,008, filed on May 20, 2003, provisional application No. 60/472,144, filed on May 20, 2003, provisional application No. 60/472,188, filed on May 20, 2003, provisional application No. 60/472,282, filed on May 20, 2003, provisional application No. 60/472,299, filed on May 20, 2003.

(51) Int. Cl.
*A61K 31/22* (2006.01)
(52) U.S. Cl. .................................... 514/551
(58) Field of Classification Search .................. 514/551
See application file for complete search history.

(56) References Cited

U.S. PATENT DOCUMENTS

| | | | |
|---|---|---|---|
| 2,456,443 | A | 12/1948 | Mueller et al. |
| 3,934,034 | A | 1/1976 | Manning |
| 4,708,964 | A | 11/1987 | Allen |
| 4,745,160 | A | 5/1988 | Churchill |
| 4,774,229 | A | 9/1988 | Jordan |
| 4,880,637 | A | 11/1989 | Jordan |
| 5,008,294 | A * | 4/1991 | Neiss et al. ............... 514/731 |
| 5,663,209 | A | 9/1997 | Huang |
| 5,827,898 | A | 10/1998 | Khandwala |
| 6,039,955 | A | 3/2000 | Sinnott |
| 6,214,874 | B1 * | 4/2001 | Huang et al. ............... 514/551 |
| 6,291,524 | B1 | 9/2001 | Huang |
| 6,365,787 | B1 | 4/2002 | Huang |
| 6,417,234 | B1 * | 7/2002 | Huang et al. ............... 514/551 |
| 6,545,019 | B2 | 4/2003 | Posmantur |
| 6,608,108 | B2 | 8/2003 | Huang |
| 6,750,247 | B2 | 6/2004 | Crews et al. |
| 6,777,444 | B2 | 8/2004 | Huang |
| 6,949,558 | B2 | 9/2005 | Altieri et al. |
| 6,958,411 | B2 | 10/2005 | Huang |
| 2003/0215409 | A1 * | 11/2003 | Quinn et al. ............... 424/70.1 |
| 2004/0014721 | A1 | 1/2004 | Hensley |
| 2004/0028758 | A1 | 2/2004 | Park et al. |
| 2004/0127562 | A1 | 7/2004 | Huang |
| 2005/0267208 | A1 | 12/2005 | Huang |

FOREIGN PATENT DOCUMENTS

WO  WO 88/03800 A1  6/1988
WO  WO 96/40090 A1  12/1996

OTHER PUBLICATIONS

Lambert et al. Tetra-O-methylnordihydroguaiaretic acid inhibits melanoma in vivo. Cancer Letters (Shannon, Ireland) (2001), 171(1), 47-56.*
John Noel Gnabre, "Isolation of anti-HIV-1 lignans from *Larrea tridentate* by counter-current chromatography," *Journal of Chromatography A*, 719:353-364 (1996).
Jih Ru Hwu, "Antiviral Activities of Methylated Nordihydroguaiaretic Acids. 1. Synthesis, Structure Identification, and Inhibition of Tat-Regulated HIV Transactivation," *J. Med. Chem.*, 41:2994-3000 (1998).
Clark W. Perry, "Synthesis of Lignans. I. Nordihydroguaiaretic Acid," *J. Org. Chem*, 37(26):4371-4376 (1972.
G. E. Amidon, "Citric Acid Monohydrate," pp. 140-142.
K. Fowler, "Diethanolamine," pp. 180-181.
P.J. Weller, "Hydrochloric Acid," pp. 238-239.
M. G. Lee, "Lactic Acid,"pp. 272-273.
C. G. Cable, "Malic Acid," pp. 311-312.
S. R. Goskonda, "Monoethanolamine," pp. 350-351.
P.J. Weller, "Potassium Citrate," pp. 429-430.
C. G. Cable, "Sodium Bicarbonate," pp. 474-477.
G. E. Amidon, "Sodium Citrate Dihydrate," pp. 482-484.
A. S. Kearney, "Sodium Phosphate, Dibasic," pp. 493-495.
V. Conway, "Sodium Phosphate, Monobasic," pp. 496-497.
K. D. Vaughan, "Tartaric Acid," pp. 558-559.
S. R. Goskonda, "Triethanolamine," pp. 572-573.
"Ionic Solutions and Electrolyte Equilibria," Chapter 17, pp. 231-249.

(Continued)

*Primary Examiner*—Kevin Weddington
(74) *Attorney, Agent, or Firm*—McDermott, Will and Emery; Michael J. Keller

(57) ABSTRACT

The present invention provides kits, methods and compositions for the treatment of tumor and other proliferative diseases such as tumors. The compositions herein contain a substantially pure preparation of at least one catecholic butane, including, for example, NDGA compounds in a pharmaceutically acceptable carrier or excipient. The catecholic butane such as NDGA or its derivatives are administered to one or more subjects in need of treatment by a route other than direct injection into the affected tissues or topical application on affected tissues.

95 Claims, 7 Drawing Sheets

OTHER PUBLICATIONS

Cathy Y. Poon, "Tonicity, Osmoticity, Osmolality, and Osmolarity," Chapter 18, pp. 250-259.

William P. Armstrong, "Clinical Modulation of Oral Leukoplakia and Protease Activity by Bowman-Birk Inhibitor Concentrate in a Phase IIa Chemoprevention Trial," *Clinical Cancer Research*, 6:4684-4691 (Dec. 2000).

K. Avgoustakis, "PLGA-mPEG nanparticles of cisplatin: in vitro nanoparticle degradation, in vitro drug release and in vivo drug residence in blood properties," *Journal of Controlled Release*, 79:123-135 (2002).

A. Beletsi, "Effect of preparative variables on the properties of poly(*dl*-lactide-coglycolide)-methoxypoly(ethyleneglycol) copolymers related to their application in controlled drug delivery," 182:187-197 (1999).

A. Branchi, "Lowering effects of four different statins on serum triglyceride level," *Eur. J. Clin. Pharmacol.*, 55:499-502 (1999).

H. Brem, "Biodegradable polymer implants to treat brain tumors," *Journal of Controlled Release*, 74:63-67 (2001).

Won Seon Choi, "Inhalation delivery of proteins from ethanol suspensions," *PNAS*, 98(20):11103-11107 (Sep. 25, 2001).

Timothy F. Cloughesy, "Intra-arterial carboplatin chemotherapy for brain tumors: A dose escalation study based on cerebral blood flow," *Journal of Neuro-Oncology*, 35:121-131 (1997).

Fernanda G. De Felice, "Inhibition of Alzheimer's disease β-amyloid aggregation, neurotoxicity, and in vivo deposition by nitrophenols: implications for Alzheimer's therapy," *The FASEB Journal*, 15:1297-1299 (May 2001).

Darius C. Desai M.D., "Serum pancreastatin levels predict response to hepatic artery chemoembolization and somatostatin analogue therapy in metastatic neuroendocrine tumors," *Regulatory Peptides*, 96:113-117 (2001).

Nancy D. Doolittle, "Safety and Efficacy of a Multicenter Study Using Intraarterial Chemotherapy in Conjunction with Osmotic Opening of the Blood-Brain Barrier for the Treatment of Patients with Malignant Brain Tumors," *Cancer*, 88(3):637-647 (Feb. 1, 2000).

James G. Drougas, "Hepatic Artery Chemoembolization for Management of Patients with Advanced Metastatic Carcinoid Tumors," *The American Journal of Surgery*, 175:408-412 (May 1998).

J. B. Epstein, "Oral topical doxepin rinse: analgesic effect in patients with oral mucosal pain due to cancer or cancer therapy," *Oral Oncology*, 37:632-637 (2001).

Joel B. Epstein, "Fluconazole mouthrinses for oral candidiasis in postirradiation, transplant, and other patients," *Oral Surgery Oral Medicine Oral Pathology*, 93(6):671-675 (Jun. 2002).

H. Fessi, "Nanocapsule formation by interfacial polymer deposition following solvent displacement," *International Journal of Pharmaceutics*, 55:R1-R4 (1989).

Alison B. Fleming, "Pharmacokinetics of the Carmustine Implant," *Clin Pharmacokinet*, 41(6):403-419 (2002.

L. Frölich, "Free Radical Mechanisms in Dementia of Alzheimer Type and the Potential for Antioxidative Treatment," *Arzneim.-Forsch./Drug Res.*, 45(1), Nr. 3a, pp. 443-446(1995).

Jie Fu, "New polymeric carriers for controlled drug delivery following inhalation or injection," *Biomaterials*, 23:4425-4433 (2002).

I. Gonda, "Inhalation delivery systems with compliance and disease management capabilities," *Journal of Controlled Release*, 53:269-274 (1998).

Maya S. Gowri, "Masoprocol Lowers Blood Pressure in Rats With Fructose-Induced Hypertension," *American Journal of Hypertension*, 12:744-746 (1999).

Jonathan D. Heller, "Tetra-O-methyl Nordihydroguaiaretic Acid Induces $G_2$ Arrest in Mammalian Cells and Exhibits Tumoricidal Activity in Vivo," *Cancer Research*, 61:5499-5504 (Jul. 15, 2001).

Carol Hermann, "Diagnostic and Pharmacological Approaches in Alzheimer's Disease," *Drugs & Aging*, 1(2):144-162 (1991).

David R. Howlett, "Inhibition of fibril formation in β-amyloid peptide by a novel series of benzofurans," *Biochem. J.*, 340:283-289 (1999) (Printed in Great Britain).

Anders G. Olsson, M.D., "A 52-Week, Multicenter, Randomized, Parallel-Group, Double-Blind, Double-dummy Study to Assess the Efficacy of Atorvastatin and Simvastatin in Reaching Low Density Lipoprotein Cholesterol and Triglyceride Targets: The Treat-to Target (3T) Study," *Clinical Therapeutics*, pp. 119-138 (Copyright © 2003 Excerpta Medica, Inc.).

Manfred Wilhelm, "Poly(styrene-ethylene oxide) Block Copolymer Micelle formation in Water: A Fluorescence Probe Study," *Macromolecules*, 24:1033-1040 (1991).

Huaihung Danny Kao, "Enhancement of the Systemic and CNS Specific Delivery of L-Dopa by the Nasal Administration of Its Water Soiluble Prodrugs," *Pharmaceutical Research*, 17(8):978-984 (2000).

Eun Hee Kim, "Roscovitine sensitizes glioma cells to TRAIL-mediated apoptosis by downregulation of surviving and XIAP," *Oncogene*, 23:446-456 (2004).

William E. Klunk, "Chrysamine-G, A Lipophilic Analogue of Congo Red, Inhibits Aβ-Induced Toxicity in PC12 Cells," *Life Sciences*, 63(20):1807-1814 (1998).

Fukashi Kohori, "Preparation and characterization of thermally responsive block copolymer micelles comprising poly(*N*-isopropylacrylamide-*b*-DL-lactide)," *Journal of Controlled Release*, 55:87-98 (1998).

Fukashi Kohori, "Control of adriamycin cytotoxic activity using thermally responsive polymeric micelles composed of poly(*N*-isopropylacrylamide-*co*-*N,N*-dimethylacrylamide)-*b*-poly(D,L-lactide)," *Colloids and Surfaces B: Biointerfaces*, 16:195-205 (1999).

Joshua D. Lambert, "Nordihydroguaiaretic acid: hepatotoxicity and detoxification in the mouse," *Toxicon*, 40:1701-1708 (2002).

Alf Lamprecht, "Biodegradable Nanoparticles for Targeted Drug Delivery in Treatment of Inflammatory flammatory Bowel Disease," *The Journal of Pharmacology and Experimental Therapeutics*, 299(2):775-781 (Copyright © 2001 by The American Society for Pharmacology and Experimental Therapeutics).

Alf Lamprecht, "Design of rolipram-loaded nanoparticles: comparison of two preparation methods," *Journal of Controlled Release*, 71:297-306 (2001).

R. T. Liggins, "Polyether-polyester diblock copolymers for the preparation of paclitaxel loaded polymeric micelle formulations," *Advanced Drug Delivery Reviews*, 54:191-202 (2002).

Giselle P. Lim, "The Curry Spice Curcumin Reduces Oxidative Damage and Amyloid Pathology in an Alzheimer Transgenic Mouse," *The Journal of Neuroscience*, 21(21):8370-8377 (Nov. 1, 2001).

P. R. Lockman, "Nanoparticle Technology for Drug Delivery Across the Blood-Brain Barrier," *Drug Development and Industrial Pharmacy*, 28(1):1-12 (2002).

Frank Loganzo, "HTI-286, a Synthetic Analogue of the Tripeptide Hemiasterlin, Is a Potent Antimicrotubule Agent that Circumvents P-Glycoprotein-mediated Resistance in Vitro and in Vivo," *Cancer Research*, 63:1838-1845 (Apr. 15, 2003).

Thomas D. Madden, "The accumulation of drugs within large unilamellar vesicles exhibiting a proton gradient: a survey," *Chemistry and Physics of Lipids*, 53:37-46 (1990).

Sankaram Mantripragada, "A lipid based depot (DepoFoam® technology) for sustained release drug delivery," *Progress in Lipid Research*, 41:392-406 (2002).

Emmeline Marttin, "Nasal Absorption of Dihydroergotamine from Liquid and Powder Formulations in Rabbits," *Journal of Pharmaceutical Sciences*, 86(7):802-807 (Jul. 1997) ( © 1997, American Chemical Society and American Pharmaceutical Association).

Russell W. McDonald, "Synthesis and anticancer activity of nordihydroguaiaretic acid (NDGA) and analogues," *Anti-Cancer Drug Design*, 16:261-270 (2001).

Alain Minn, "Drug Transport into the Mammalian Brain: The Nasal Pathway and its Specific Metabolic Barrier," *Journal of Drug Targeting*, 10(4):285-296 (2002).

L. Mu, "A novel controlled release formulation for the anticancer drug paclitaxel (Taxol®): PLGA nanoparticles containing vitamin E TPGS," *Journal of Controlled Release*, 86:33-48 (2003).

Kenjiro Ono, "Nordihydroguaiaretic acid potently breaks down preformed Alzheimer's β-amytoid fibrils in vitro," *Journal of Neurochemistry*, 81:434-440 (2002).

F.-A. Pitten, "Do cancer patients with chemotherapy-induced leucopenia benefit from an antiseptic chlorhexidine-based oral rinse? A double-blind, block-randomized controlled study," *Journal of Hospital Infection*, 53:283-291 (2003).

Natalya Y. Rapoport, "Micellar delivery of doxorubicin and its paramagnetic analog, ruboxyl, to HL-60 cells: effect of micelle structure and ultrasound on the intracellular drug uptake," *Journal of Controlled Release*, 58:153-162 (1999).

M. J. Reed, "Effect of masoprocol on carbohydrate and lipid metabolism in a rat model of Type II diabetes," *Diabetologia*, 42:102-106 (1999).

Lon S. Schneider, M.D., "New Therapeutic Approaches to Cognitive Impairment," *J. Clin Psychiatry*, 59(11):8-13 (1998).

Uma S. Sharma, "Liposome-Mediated Therapy of Intracranial Brain Tumors in a Rat Model," *Pharmaceutical Research*, 14(8):992-998 (1997).

C. X. Song, "Formulation and characterization of biodegradable nanoparticles for intravascular local drug delivery," *Journal of Controlled Release*, 43:197-212 (1997).

Milan Stuchlik, "Lipid-Based Vehicle for Oral Drug Delivery," *Biomed. Papers*, 145(2):17-26 (2001).

Fatih M. Uckun, "Treatment of Therapy-Refractory B-Lineage Acute Lymphoblastic Leukemia with an Apoptosis-inducing CD19-directed Tyrosine Kinase Inhibitor," *Clinical Cancer Research*, 5:3906-3913 (Dec. 1999).

Da Li Wang, "Topical Delivery of 13-*cis*-Retinoic Acid by Inhalation Up-Regulates Expression of Rodent Lung but not Liver Retinoic Acid Receptors," *Clinical Cancer Research*, 6:3636-3645 (Sep. 2000).

Xichen Zhang, "Development of amphiphilic diblock copolymers as micellar carriers of taxol," *International Journal of Pharmaceutics*, 132:195-206 (1996) ( © 1996 Elsevier Science B.V.).

Merck Research Laboratories, The Merck Manual of Diagnosis and Therapy, 17th Ed., 1999, pp. 986-995.

Lieberman, S.V., et al, A Synthesis of Nordihydroguaiaretic Acid, Cf, Organic Synthesis, vol. 69, pp. 1540-1541, Wyeth Inst. of Applied Biochemistry, Philadelphia Jan. 17, 1947.

Schrecker, Anthony W. , Meso-Dihydroguaiaretic Acid and its Derivatives. The Laboratory of chemical Pharmacology, National Cancer Institute, pp. 3823-3827, Jul. 20, 1957.

Whitman, Stephanie, et al.., "Structure-Activity Relationship Studies of Nordihydroguaiaretic Acid Inhibitors Toward Soybean, 12-Human, and 15-Human Lipoxygenase." J. Med. Chem. 2002, 45, pp. 2659-2661.

Khanna, Niharika, "Phase I Clinical Trial of Repeat Dose Terameprocol Vaginal Ointment in Healthy Female Volunteers." Sexually transmitted Diseases, Dec. 2008, vol. 35, pp. 1-6.

Khanna, Niharika, "Phase I/II Clinical Safety Studies of Terameprocol Vaginal Ointment." Gynecologic Oncology, 107 (2007), pp. 554-562.

Chang, Chih-Chuan, et al, Reversal of Multidrug Resistance by Two Nordihydroguaiaretic Acid Derivatives, M4N and Maltose-M3N, and Their Use in Combination with Doxorubicin or Paclitaxel. Cancer Chemotherapy Pharmacology (2006) DOI 10.1007/s00280-006-0214-9.

Hansel, Donna E., at al., CDC2/CDK1 Expression in Esophageal Adenocarcinoma and Precursor Lesions Serves as a Diagnostic and Cancer Progression Marker and Potential Novel Drug Target. Am. J. Surg. Pathol., vol. 29, No. 3, Mar. 2005, pp. 390-399.

Lambert, Joshua D., et al., Tetra-O-Methylnordihydroguaiaretic Acid Inhibits Melanoma in Vivo. Cancer Letters, 171 (2001) pp. 47-56.

Lopez, Rocio A., et al., The Anticancer Activity of the Transcription Inhibitor Terameprocol (meso-tetra-O-methyl nordihydroguaiaretic acid) Formulated for Systemic Administration. Anti-Cancer Drugs, 2007, vol. 18 No. 8, pp. 933-939.

Park, Richard, et al., Systemic Treatment with Tetra-O-Methyl Nordihydroguaiaretic Acid Suppresses the Growth of Human Zenograft Tumors. Clin. Cancer Res. 2005; 11 (12), Jun. 15, 2005, pp. 4601-4609.

Mak, Duncan H., et al., Tetra-O-methyl Nordihydroguaiaretic Acid Inhibits Growth and Induces Death of Leukemia Cells Independent of Cdc2 and Survivin. Leukemia & Lymphoma, Jan. 20, 2007, pp. 1-12.

Huang, Ru Chih C., et al., Survivin-Dependent and -Independent Pathways and the Induction of Cancer Cell Death by Tetra-O-methyl Nordihydroguaiaretic Acid. Seminars in Oncology, 2006, 04.010, pp. 479-485.

Chen, Hongshan, et al., Antiviral Activities of Methylated Nordihydroguaiaretic Acids. 2. Targeting Herpes Simplex Virus Replication by the Mutation Insensitive Transcription Inhibitor Tetra-O-methyl-NDGA. J. Med. Chem. 1998, 41, pp. 3001-3007.

Craigo, Jodi, Inhibition of Human Papillomavirus Type 16 Gene Expression by Nordihydroguaiaretic Acid Plant Lignan Derivatives Antivral Research 47 (2000), pp. 19-28.

Chang, Chih-Chuan, et al., "Tetra-O-methyl nordihydroguaiaretic acid induces growth arrest and cellular apoptosis by inhibiting Cdc2 and survivin expression," PNAS, vol. 101 No. 36, Sep. 7, 2004, pp. 13239-13244.

Lerner, Aaron B., M.D., "Should Vitiligo Be Induced in Paients After Resection of Primary Melanoma?" Arch Dermatol-vol. 113, p. 421, Apr. 1977.

Smart, C.R., "An Interesting Observation on Nordihydroguaiaretic Acid (NSC-4291), NDGA) and a Patient with Malignant Melanoma-A Preliminary Report." Cancer Chemotherapy Reports, Part 1, vol. 53, No. 2, Apr. 1969, pp. 147-151.

Paslin, David, "Melanoma Treatment with Phenolic or Catecholic Compounds," Arch. Dermatol., vol. 113, Sep. 1977, p. 1302.

McCormick, David L., "Nordihydroguaiaretic Acid Suppression of Rat Mammary Carcinogenesis Induced by N-Methyl-N-Nitrosourea." Cancer Letters, 37 (1987) 139-146. Elsevier Scien.

Birkenfeld, Shlomo, "Antitumor Effects of Inibitors of Arachidonic Acid Cascade on Experimentally Induced Intestinal Tumors," Dis. Colon Rectum, 1987, vol. 30,1, pp. 43-46.

Wilson, Diana E., "Effect of nordihydroguaiaretic acid on cultured rat and human glioma cell proliferation." J. Neurosurg 71:551-557, 1989.

Ansar, Sabah, "Nordihydroguairetic acid is a potent inhibitor of ferric-nitrilotriacetate-mediated hepatic and renal toxicity, and renal tumour promotion, in mice." Carcinogenesis, vol. 20, No. 4, pp. 599-606, 1999.

Steele, Vernon E., "Lipoxygenase Inhibitors as Potential Cancer Chemopreventives." Cancer Epidemiology, Biomarkers & Prevention, vol. 8, pp. 467-483, May 1999.

Lambert, Joshua D., "Pharmacokinetic analysis by high-performance liquid chromatography of intravenous nordihydroguaiaretic acid in the mouse." Journal of Chromatography B, 754 (2001), pp. 85-90.

Walker, Jennifer L., "5-Lipoxyenase and human pulmonary artery endothelial cell proliferation." Am. J. Physiol. Heart Circ. Physiol. 282:H585-H593, 2002.

Tong, Wei-Gang, "Lipoxygenase Inhibitors Attenuate Growth of Human Pancreatic Cancer Xenografts and Induce Apoptosis through the Mitochondrial Pathway." Molecular Cancer Therapeutics, vol. 1, pp. 929-935, Sep. 2002.

Seufferlein, T., "Mechanisms of nordihydroguaiaretic acid-induced growth inhibition and apoptosis in human cancer cells." British Journal of Cancer (2002) 86, pp. 1188-1196.

Hausott, B., "Naturally occurring lignans efficiently induce apoptosis in colorectal tumor cells." J. Cancer Res. Clin. Oncol. (2003) 129:pp. 569-576.

Claudia, Anesini, "In Vivo" and "In Vitro" Antitumoral Action of Larrea Divaricata Cay. APPTLA 46, pp. 33-40, 1996.

Iida, N., "Suppression of arachidonic acid cascade-mediated apoptosis in aflatoxin B1-induced rat hepatoma cells by glucocrticoids." Carcinogenesis, vol. 19, No. 7, pp. 1191-1202, 1998.

Lambert, Joshua D., "Nordihydroguaiaretic Acid: A Review of Its Numerous and Varied Biological Activities." Pharmaceutical Biology 2004, vol. 42 No. 2, pp. 149-158.

Jakovljevic, V.L., "The Effects of Nitric Oxide Synthase—versus Lipoxygenase Inhibition on Coronary Flow and Nitrite Outflow in Isolated Rat Heart." Gn. Physiol. Biophys. (2005), 24, pp. 199-207.

Nie, Daotai, "Mechanisms Regulating Tumor Angiogenesis by 12-Lipoxygenase in Prostate Cancer Cells." Journal of Biological Chemistry, Vo 281, No. 27, pp. 18601-18609, Jul. 7, 2006.

Blecha, J.E., "Inhibition of IGF-1R and lipoxygenase by nordihydroguaiaretic acid (NDGA) analogs." J. Bioorganic & Medicinal Chemistry Letters, 17 (2007) pp. 4026-4029.

Ryan, C.J., "A pilot dose-escalation study of the effects of nordihydroguareacetic acid on hormone and prostate specific antigen levels in patients with relapsed prostate cancer." Journal Compilation, 2008 BJU International, 101, pp. 436-439.

Meyer, Gery E., "Nordihydroguaiaretic Acid Inhibits Insulin-like Growth Factor Signaling, Growth, and Survival in Human Neuroblastoma Cells." Journal of Cellular Biochemistry 102:1529-1541 (2007).

Kim, So Yong, "Regulation of pro-inflammatory responses by lipoxygenases via intracellular reactive oxygen species in vitro and in vivo." Experimental and Molecular Medicine, vol. 40, No. 4, pp. 461-476, Aug. 2008.

Ryan, C.J., "Inhibitory Effects of Nordihydroguaiaretic Acid (NDGA) on the IGF-I Receptor and Androgen Dependent Growth of LAPC-4 Prostate Cancer Cells." The Prostate. 68:1232-1240 (2008).

Reed, et al, 1999, "Effect of masoprocol on carbohydrate and lipid metabolism in a rat model of Type II diabetes." Diebetologia 42(1), Abstract. << www.ncbi.nim.nih.gov/pubmed/1002758>> Last accessed Oct. 12, 2009.

Chen Xiaoxin et al: "Aberrant arachidonie acid metabolism esophageal adenocarcinogenesis, and the effects of sulindac, nordihydroguaiaretic acid, and alpha-difluoromethylornithine on tumorigenesis in a rat surgical model." Carcinogenesis (Oxford), vol. 23, No. 12, Dec. 2002, pp. 2095-2102.

Steren, Edgar D. "Lymphokine-Activated Killer Cell Induction in Tumor-Infilltrating Leukocytes From Colon Cancer Patients," Cancer, Dec. 1, 1989, vol. 64, pp. 2232-2242.

Snydar. David S., Antiproliferative Effects of Lipoxyganase inhibitors on Malignant Human Hematopoietic Cell Lines, Exp. Hemoto. 17:6-9 (1989).

Wan, Zhi Y., "Antimutagenic and antitumorignic activities of nordihydroguaiaretic acid." Mutation Research, 261 (1991) 153-162.

Yu, Akinori, "Antipromoting Effect of Nordihydroguaiaretic Ackl on N-Butly-N-(4-hydroxybutyl) nitrosamine and Sodium Saccharin-induced Rat Urinary Bladder Carcinogenesis." Jpn. J. Cancer Ses. 83, 944-948, Sep. 1992.

Zamora, John M. "A Comparison of the Cytotoxicity of Nordihydroguaearetic Acid and its Derivatieves." Journal of the Tessennee Academy of Science, 67(4): 77-80, Oct. 1992.

Shi, Liming, et al., "Effect of NDGA Beef Heart Mitochondria and EMT6 Mouse Mammary Carcinoma Cells." Research Communications in Molecular Pathology and Pharmacology, vol. 90, No. 2 pp. 235-254, Nov. 1995.

Avis, Ingalill M., "Growth Control of Lung Cancer by Intruption of 5-Lipoxgenase-mediated Growth Factor Signaling." The Journal of Clinical Investigation, vol. 97, No. 3, Feb. 1996 pp. 806-813.

* cited by examiner

A. Sites of Major M4N Accumulation

B. Sites of Minor M4N Accumulation

B. Control Vs. M4N-Treated Female Mice

A. Control Vs. M4N-Treated Male Mice

TA in DMSO - Serum Results

METHODS FOR DELIVERY OF CATECHOLIC BUTANES FOR TREATMENT OF TUMORS

CROSS-REFERENCE TO RELATED APPLICATIONS

This application is a continuation of International Patent Application No. PCT/US2004/016235, filed May 20, 2004, and published in the English language as International Publication No. WO 2005/007080 on Jan. 27, 2005, which claims priority to U.S. provisional application No. 60/472,008, filed May 20, 2003; U.S. provisional application No. 60/472,144, filed May 20, 2003; U.S. provisional application No. 60/472,188, filed May 20, 2003; U.S. provisional application No. 60/472,282, filed May 20, 2003; and U.S. provisional application No. 60/472,299, filed May 20, 2003; the contents of all of which are incorporated herein by reference in their entireties.

BACKGROUND OF THE INVENTION

This invention relates to kits, methods and compositions containing catecholic butanes for the delivery of such to subjects for the treatment of malignant, premalignant and benign tumors. This invention also relates to methods of making the foregoing compositions. In such methods of treatment, one or more catecholic butanes are administered to subjects via routes of delivery other than direct injection into the affected tissue, and other than topical application onto the affected tissue. This invention further relates to compositions comprising one or more catecholic butanes that are formulated appropriately for such modes of delivery and treatment.

Catecholic butanes, including nordihydroguaiaretic acid ("NDGA") and its derivatives, have been used for the inhibition of tumor growth in certain experimental animals. For example, Jordan et al. in U.S. Pat. No. 5,008,294 described the use of a single dose of NDGA on a mammary carcinoma MX-1 xenograft in athymic nude NCr mice. In one experiment, NDGA was injected into the tumor one day following subcutaneous implantation of a 14 mg fragment of the human mammary carcinoma in the axillary region of the mice. Jordan et al. further described topical application of NDGA after day 23 of implantation of human breast adenocarcinomas in athymic mice. Some evidence of inhibition of tumor growth was observed in those experiments, but it is unclear whether the antitumor effect was durable.

Huang et al. in U.S. Pat. No. 6,417,234 and U.S. Pat. No. 6,214,874 described intratumor injection of a NDGA derivative, designated tetra-O-methyl NDGA or $M_4N$, and another NDGA derivative, designated $G_4N$, separately or together into mice implanted with HPV-16 transformed immortal mouse epithelial cells (C3). Huang et al. also found some evidence of suppression of tumor growth by these NDGA derivatives. It is unknown whether compounds such as these NDGA derivatives can be safely administered to other animals such as humans.

Certain of the catecholic butanes, such as $M_4N$, which is a NDGA derivative, are hydrophobic compounds found to be soluble in dimethyl sulfoxide ("DMSO"). When the composition of $M_4N$ in DMSO was injected into the tumor, the composition appeared to penetrate most but not all of the tumor tissues. A possible explanation may be that the hydrophobic nature of the compound limits its penetration. It would be desirable if a formulation can be found for safe systemic administration of these hydrophobic compounds so as to improve their efficacy, expand their utility and yet maintain their biological activities, such as anti-tumor activities. It would further be desirable if the catecholic butanes, including the NDGA Compounds, can be safely administered by routes of administration other than by direct injection into the affected tissues or by topical application.

Moreover, intratumor injection or direct injection of drugs into affected tissues may not be an ideal treatment regimen. Patients sometimes experience injection site discomfort. In addition, many tumors are not amenable to intratumor injection of a therapeutic, and many may not respond to topical application of a therapeutic. It would be desirable if a different route of administration of these catecholic butanes can be found that would be safe and appropriate for the disease or condition and yet maintain the biological activities of such compounds.

Additionally, it is not known whether the catecholic butanes, including NDGA and NDGA derivatives (collectively, the "NDGA Compounds"), or formulations containing them can differentially inhibit the growth or progression of tumor growth in humans without adversely affecting normal tissues. It would be desirable if the catecholic butanes, including the NDGA Compounds can be formulated and administered in such a way as to spare the normal tissues of any adverse effects.

Further, a majority of human malignant tumors are both local and systemic in nature in that the primary malignant tumors are produced locally whereas the secondary tumors, seeded from the primary, are spread systemically to other tissues, or arise de novo from tissues similar to the source of the primary. The most appropriate therapeutic options, therefore, include those that deliver effective medication to the primary source of malignancy as well as to the secondary sources. It would be desirable if an effective therapeutic can be formulated that can access both the primary and secondary sources of malignancies.

It would also be desirable if the NDGA derivatives can be formulated in a manner that would facilitate delivery to targeted tissues and maintenance of a certain range of dose level in the targeted tissues.

BRIEF SUMMARY OF THE INVENTION

It is, thus, one of the objects of the present invention to provide methods and compositions for the prevention or treatment of tumors such as to address the problems in the prior art methods and compositions, for example, those described in the Background.

It is another one of the objects of the present invention to provide methods and compositions as above, such as, for example, to inhibit the growth, development or progression of tumors.

It is another one of the objects of the present invention to provide one or more methods of administering the catecholic butanes, including the NDGA Compounds, that are effective in the prevention or treatment of tumors as above, where the targeted tissues or the affected tissues to be treated are not easily accessible to direct injection or amenable to topical application of such compounds.

It is a further one of the objects of the present invention to provide one or more formulations containing the catecholic butanes, including the NDGA Compounds, that can facilitate and/or optimize distribution of the catecholic butanes, including the NDGA Compounds, to the targeted tissues.

It is another one of the objects of the present invention to provide compositions containing one or more catecholic butanes, including the NDGA Compounds, in formulations appropriate for treatment of the targeted tissues.

In accordance to one of the objects of the present invention, there is provided a pharmaceutical composition for treatment of a disease in a subject, such as an animal, for example, a human, where the composition contains at least one catecholic butane and a pharmaceutically acceptable carrier or excipient, and where the composition is formulated for administration by a route other than by direct injection into or topical application onto an affected tissue.

In accordance to another one of the objects, there is provided a composition as above, where the disease, disorder or condition is other than an inflammatory disease, for example, other than an inflammatory disease that is associated with microglial cell activation or stimulation.

In accordance to another one of the objects, there is provided a composition as above, where the disease is a proliferative disease. Such a proliferative disease may be a malignant tumor, a premalignant condition, or a benign tumor.

In accordance to a further one of the objects, there is provided a composition as above, where the disease results from or is associated with a virus infection, such as, for example, HIV infection, HPV infection, or HSV infection.

In accordance to still another one of the objects, there is provided a composition as above, where the composition is formulated for intranasal administration, oral administration, including through slow release or rapid release capsules, for inhalation, for subcutaneous administration, for transdermal administration, for intra-arterial administration, with or without occlusion, for intracranial administration, intraventricular administration, intravenous administration, buccal administration, intraperitoneal administration, intraocular administration, central venous administration, intramuscular administration or for implantation.

In accordance to another one of the objects, there is provided a composition as above, where the pharmaceutically acceptable carrier or excipient contains dimethyl sulfoxide (DMSO), phosphate buffered saline (PBS), saline, an oil such as, for example, castor oil or corn oil, Cremaphor EL, and ethanol or a mixture containing one or more of such.

In accordance to another one of the objects, there is provided a composition as above, where the pharmaceutically acceptable carrier or excipient contains a lipid based formulation, a liposomal formulation, a nanoparticle formulation, a micellar formulation, a water soluble formulation, a Cremaphor EL/ethanol/saline formulation or any of the foregoing in a biodegradable polymer.

In accordance to yet another one of the objects, there is provided a composition as above, where the catecholic butane has the structural formula I as follows:

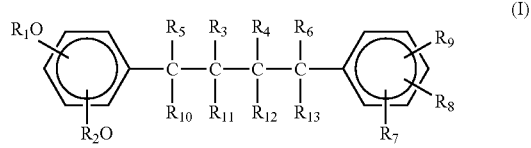

where $R_1$ and $R_2$ are independently —H, a lower alkyl, a lower acyl, an alkylene or an unsubstituted or substituted amino acid residue or salt thereof; $R_3$, $R_4$, $R_5$, $R_6$, $R_{10}$, $R_{11}$, $R_{12}$ and $R_{13}$ are independently —H or a lower alkyl; and $R_7$, $R_8$ and $R_9$ are independently —H, —OH, a lower alkoxy, a lower acyloxy, or any two adjacent groups together may be an alkyene dioxy, or an unsubstituted or substituted amino acid residue or salt thereof.

In accordance to still another one of the objects, there is provided a catecholic butane as above, where $R_1$ and $R_2$ independently —H, a lower alkyl, a lower acyl, or an unsubstituted or substituted amino acid residue or salt thereof; $R_3$, $R_4$, are independently a lower alkyl; $R_5$, $R_6$, $R_{10}$, $R_{11}$, $R_{12}$ and $R_{13}$ are independently —H; and $R_7$, $R_8$ and $R_9$ are independently —H, —OH, a lower alkoxy, a lower acyloxy, or unsubstituted or substituted amino acid residue or salt thereof.

In accordance to yet another one of the objects, there is provided a catecholic butane as above, where $R_1$ and $R_2$ are independently —H, a lower alkyl, a lower acyl, or an unsubstituted or substituted amino acid residue or salt thereof; $R_3$, $R_4$, are independently a lower alkyl; $R_5$, $R_6$, $R_7$, $R_{10}$, $R_{11}$, $R_{12}$ and $R_{13}$ are independently —H; and $R_8$ and $R_9$ are independently —OH, a lower alkoxy, lower acyloxy, or an unsubstituted or substituted amino acid residue or salt thereof.

In accordance to still another one of the objects, there is provided the catecholic butane as above, where $R_1$ and $R_2$ are independently —$CH_3$ or —$(C=O)CH_2N(CH_3)_2$ or a salt thereof.

In accordance to still another one of the objects, there is provided the catecholic butane as above, where $R_8$ and $R_9$ are independently —$OCH_3$ or —$O(C=O)CH_2N(CH_3)_2$ or a salt thereof.

In accordance to still another one of the objects, there is provided the catecholic butane as above, where $R_1$ and $R_2$ are independently —$CH_3$, —$(C=O)CH_2N(CH_3)_2$ or —$(C=O)CH_2N^+H(CH_3)_2.Cl^-$ and $R_8$ and $R_9$ are independently —$OCH_3$, —$O(C=O)CH_2N(CH_3)_2$ or —$O(C=O)CH_2N^+H(CH_3)_2.Cl^-$.

In accordance to still another one of the objects, there is provided the catecholic butane as above, where $R_1$ and $R_2$ are independently —H or —$CH_3$ and $R_8$ and $R_9$ are independently —OH or —$OCH_3$, provided that the catecholic butane is not NDGA.

In accordance to still another one of the objects, there is provided the catecholic butane as above, where $R_1$ and $R_2$ are independently —$CH_3$ and $R_8$ and $R_9$ are independently —$OCH_3$.

In accordance to still another one of the objects, there is provided the catecholic butane as above, where the catecholic butane is NDGA.

In accordance to still another one of the objects, there is provided the catecholic butane as above, where the catecholic butane is other than NDGA.

In accordance to yet another one of the objects, there is provided a method of making a pharmaceutical composition containing a catecholic butane, where the method includes the steps of (a) providing a catecholic butane as above; (b) providing a pharmaceutically acceptable carrier or excipient as above, and (c) combining the catecholic butane with the pharmaceutically acceptable carrier or excipient.

In accordance to a further one of the objects of the present invention, there is provided a method of treating a disease in a subject, where the method of treatment includes providing a pharmaceutical composition as above and administering the composition to the subject by a route other than by direct injection into the tumor or topical application onto the tumor.

In accordance to another one of the objects, there is provided a method of treatment as above, where the disease is other than an inflammatory disease, for example, other than an inflammatory disease that is associated with microglial cell activation or stimulation.

In accordance to another one of the objects, there is provided a method of treatment as above, where the disease is a proliferative disease such as a malignant tumor, a premalignant condition, or a benign tumor.

In accordance to a further one of the objects, there is provided a method of treatment as above, where the disease results from or is associated with a virus infection, such as, for example, HIV infection, HPV infection, or HSV infection.

In accordance to still another one of the objects, there is provided a method of treatment as above, where the composition is formulated for intranasal administration, oral administration, including through slow release or rapid release capsules, for inhalation, for subcutaneous administration, for transdermal administration, for intra-arterial administration, with or without occlusion, for intracranial administration, intraventricular administration, intravenous administration, buccal administration, intraperitoneal administration, intraocular administration, central venous administration, intramuscular administration or for implantation.

In accordance to another one of the objects, there is provided a method of treatment as above, where the pharmaceutically acceptable carrier or excipient contains dimethyl sulfoxide (DMSO), phosphate buffered saline (PBS), saline, an oil such as, for example, castor oil or corn oil, Cremaphor EL, ethanol and any combination of such.

In accordance to another one of the objects, there is provided a method of treatment as above, where the pharmaceutically acceptable carrier or excipient contains a lipid based formulation, a liposomal formulation, a nanoparticle formulation, a micellar formulation, a water soluble formulation, a Cremaphor EL/ethanol/saline formulation or any of the foregoing in a biodegradable polymer.

In accordance to yet another one of the objects, there is provided a method of treatment as above, where the catecholic butane has a formula given above.

In accordance to yet another one of the objects, there is provided a method of treatment as above, where the catecholic butane is tetra-O-methyl NDGA.

In accordance to still another one of the objects, there is provided a method of treatment as above, where the catecholic butane is tetra-dimethylglycinyl NDGA.

In accordance to another one of the objects, there is provided a method of treatment as above, where the catecholic butane is tri-O-methyl NDGA.

In accordance to still another one of the objects, there is provided a method of treatment as above, where the catecholic butane is NDGA.

In accordance to another one of the objects, there is provided a method of treatment as above, where the catecholic butane is other than NDGA.

In accordance to another one of the objects, there is provided a method of treatment as above, where the method includes administering at least two catecholic butanes.

In accordance to another one of the objects, there is provided a method of treatment as above, where the two catecholic butanes are administered substantially contemporaneously.

In accordance to another one of the objects, there is provided a method of treatment as above, where the two catecholic butanes are administered at different times.

In accordance to another one of the objects, there is provided a method of treatment as above, where the two catecholic butanes are selected from the group consisting of tetra-O-methyl NDGA, tri-O-methyl NDGA and tetra-dimethylglycinyl NDGA.

In accordance to another one of the objects, there is provided a method of treatment as above, where the nanoparticle formulation contains at least one selected from the group consisting of poly(DL-lactide-co-glycolide), poly vinyl alcohol, d-α-tocopheryl polyethylene glycol 1000 succinate, and poly(lactide-co-glycolide)-monomethoxy-poly(polyethylene glycol).

In accordance to another one of the objects, there is provided a method of treatment as above, where the liposomal formulation comprises at least one selected from the group consisting of phosphatidylcholine/cholesterol/PEG-DPPE, distearoylphosphatidylcholine/cholesterol/PEG-DPPE, and 1-2-dioleoyl-sn-glycero-3-phosphocholine/1-2-dipalmitoyl-sn-glycero-3-phospho-rac-(1-glycerol) sodium salt/cholesterol/triolein/tricaprylin.

In accordance to another one of the objects, there is provided a method of treatment as above, where the disease is cancer and the cancer is a solid tumor, a lymphoma or leukemia.

In accordance to another one of the objects, there is provided a method of treatment as above, where the cancer is selected from the group consisting of malignant, pre-malignant or benign brain tumor, nasal pharyngeal tumor, head and neck tumor, liver tumor, kidney tumor, prostate tumor, breast tumor, a bladder tumor, pancreatic tumor, stomach tumor, colon tumor, ovarian tumor, cervical tumor, and skin tumor and metastases thereto.

In accordance to another one of the objects, there is provided a method of treatment as above, where the method comprises administering the composition more than once.

In accordance to another one of the objects, there is provided a method of treatment as above, where the pharmaceutically acceptable carrier or excipient is an aqueous preparation.

In accordance to another one of the objects, there is provided a method of treatment as above, where the pharmaceutically acceptable carrier or excipient comprises a hydrophobic preparation.

In accordance to another one of the objects, there is provided a method of treatment as above, where the hydrophobic preparation comprises a lipid based vehicle.

In accordance to another one of the objects, there is provided a method of treatment as above, where the pharmaceutically acceptable carrier or excipient comprises at least one selected from the group consisting of castor oil, peanut oil, dimethyl sulfoxide (DMSO), and other dietary fats or oils.

In accordance to another one of the objects, there is provided a method of treatment as above, where the composition is formulated in the form of one selected from the group consisting of a tablet, a powder, a gel capsule, a liquid, and an oral rinse.

In accordance to another one of the objects, there is provided a method of treatment as above, where the pharmaceutically acceptable carrier or excipient comprises a polymer formulation.

In accordance to another one of the objects, there is provided a method of treatment as above, where the polymer formulation is a biodegradable polymer formulation.

In accordance to another one of the objects, there is provided a method of treatment as above, where the pharmaceutically acceptable carrier or excipient allows for high local drug concentration and sustained release over a period of time.

In accordance to another one of the objects, there is provided a method of treatment as above, where the polymer formulation comprises at least one selected from the group consisting of 1,3-bis(p-carboxyphenoxy) propane, sebacic acid, poly(ethylene-co-vinyl acetate), and poly(lactide-co-glycolide).

In accordance to another one of the objects, there is provided a method of treatment as above, where the catecholic butane is dissolved in saline, DMSO or ethanol prior to administration.

In accordance to another one of the objects, there is provided a method of treatment as above, where the composition is at least one selected from the group consisting of: a powder, an aerosol, an aqueous formulation, a liposomal formulation, a nanoparticle formulation, and a hydrophobic formulation.

In accordance to another one of the objects, there is provided a method of treatment as above, where the composition is administered daily for a defined period of time.

In accordance to another one of the objects, there is provided a method of treatment as above, where the composition is administered intermittently.

In accordance to another one of the objects, there is provided a method of treatment as above, where the catecholic butane is infused into the subject.

In accordance to another one of the objects, there is provided a method of treatment as above, where the catecholic butane is a water soluble compound.

In accordance to another one of the objects, there is provided a method of treatment as above, where the catecholic butane is a hydrophobic compound.

In accordance to another one of the objects, there is provided a method of treatment as above, where the catecholic butane is formulated as a liquid, an aerosol, an oral rinse, a suspension, a tablet, a powder, or a gel capsule.

In accordance to yet one of the objects, there is provided a method of treatment of a viral infection in a subject comprising administering the composition of claim 1 to the subject, wherein the viral infection results from or is associated with HIV, HPV, or HSV.

In accordance to another one of the objects, there is provided a method of treatment as above, where the catecholic butane is administered in a range of greater than about 10 mg/kg and less than about 375 mg/kg per dose into humans.

In accordance to another one of the objects, there is provided a method of treatment as above, where the range is greater than about 10 mg/kg and less than about 250 mg/kg per dose.

In accordance to another one of the objects, there is provided a method of treatment as above, where the range is greater than about 10 mg/kg and less than about 200 mg/kg per dose.

In accordance to another one of the objects, there is provided a method of treatment as above, where the range is greater than about 10 mg/kg and less than about 150 mg/kg per dose.

In accordance to another one of the objects, there is provided a method of treatment as above, where the range is greater than about 10 mg/kg and less than about 100 mg/kg per dose.

In accordance to another one of the objects, there is provided a method of treatment as above, where the range is greater than about 10 mg/kg and less than about 75 mg/kg per dose.

In accordance to another one of the objects, there is provided a method of treatment as above, where the range is greater than about 10 mg/kg and less than about 50 mg/kg per dose.

In accordance to another one of the objects, there is provided a method of treatment as above, where the composition is administered systemically, such as intravenously, for example.

In accordance to another one of the objects, there is provided a method of treatment as above, where the catecholic butane is tri-O-NDGA or tetra-O-methyl NDGA.

In accordance to still one of the objects, there is provided a kit for treatment of a disease comprising the pharmaceutical composition above and instructions for administration of the composition.

In accordance to a further one of the objects, there is provided a method of treating a tumor in a subject, where the tumor is a malignant, premalignant or benign tumor, and where the tumor arises from or is associated with a tissue or organ selected from the group consisting of: breast, liver, stomach, pancreas, colorectal, colon and prostate, comprising the steps of: (a) providing a composition containing tetra-O-methyl NDGA ($M_4N$) and a pharmaceutically acceptable carrier or excipient; and (b) administering the composition to the subject; where the composition is administered other than by direct injection into or topical application onto the tumor.

In accordance to a further one of the objects, there is provided a method of treating a tumor as above, where the method includes administering the composition orally, where the oral compositon may be a slow release formulation or a rapid release formulation.

In accordance to a further one of the objects, there is provided a method of treating a tumor as above, where the pharmaceutically acceptable carrier or excipient is an oil, such as, for example, castor oil or corn oil.

In accordance to a further one of the objects, there is provided a method of treating a tumor as above, where the composition is present in an edible mix.

In accordance to a further one of the objects, there is provided a method of treating a tumor as above, where the catecholic butane composition is administered daily for a period of time, such as, for example, daily for 5 or more days to a week, or daily for 5 or more days to 2 weeks, or daily for 5 or more days to 3 weeks.

In accordance to a further one of the objects, there is provided a method of treating a tumor as above, where the amount of tetra-O-methyl NDGA administered is at least 30 mg per dose, or optionally, at least 90 mg per dose.

In accordance to a still further one of the objects, there is provided a method of treating a tumor as above, where tetra-O-methyl NDGA is present in the composition at a concentration of 20 mg/mL.

In accordance to a further one of the objects, there is provided a method of treating a tumor as above, where the pharmaceutically acceptable carrier or excipient comprises Cremaphor EL, ethanol and saline, where Cremaphor EL may be present at a concentration of about 6%, ethanol may be present at a concentration of about 6%, and saline may be present at a concentration of about 88%, for example.

In accordance to another one of the objects, there is provided a method of treating a tumor as above, where the composition administered to the subject comprises at least 2 mg of tetra-O-methyl NDGA per dose.

In accordance to a further one of the objects, there is provided a method of treating a tumor as above, where the composition is administered intravenously or intraperitoneally.

In accordance to a still another one of the objects, there is provided a method of treating a tumor as above, where the composition is administered more frequently than once every 6 days for a period of time or optionally, more frequently than once every 2 days for a period of time.

Further objects, features and advantages of the present invention will be apparent to one of ordinary skill in the art upon reading the present description. Such other objects, features, and advantages are also deemed embodied by the present invention.

BRIEF DESCRIPTION OF THE SEVERAL VIEWS OF THE DRAWINGS

The foregoing summary, as well as the following detailed description of the invention, will be better understood when read in conjunction with the appended drawings.

In the drawings:

FIG. 1A represents the quantity of $M_4N$, in micrograms per gram of tissue, found in each organ containing a relatively high quantity of $M_4N$. FIG. 1B represents those organs containing a relatively low quantity of $M_4N$.

Figure 1:
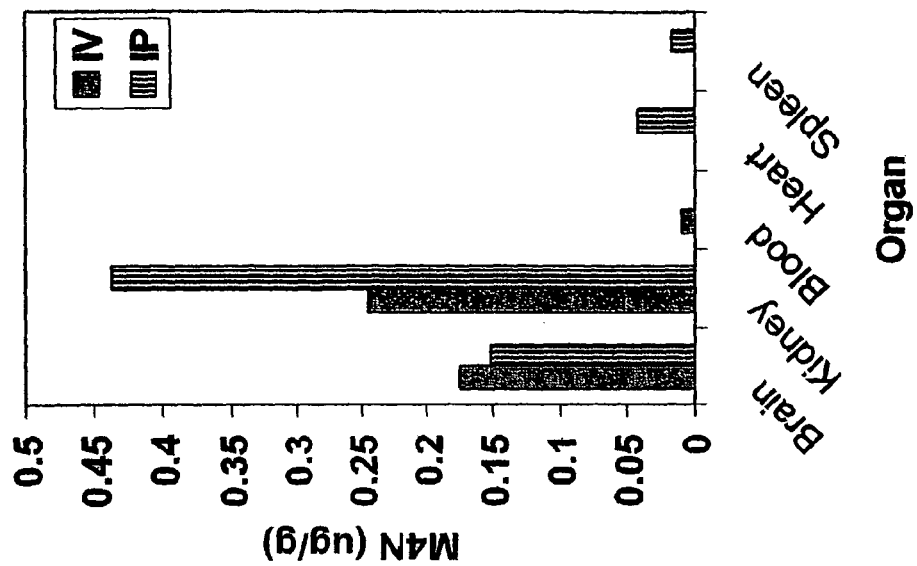
FIG. 1 shows systemic distribution of $M_4N$ to various organs at 3 hours following intravenous and intraperitoneal injection. Mice were injected with 100 μCi of $^3H$-$M_4N$ and 60 mM of unlabeled $M_4N$. Organs and blood were harvested and weighed at 3 hours post-injection and the $M_4N$ was extracted. The tritium content of the organ extracts were measured, and the quantity of $M_4N$ in each organ was calculated based on the specific activity of the inoculum.
Figure 1:
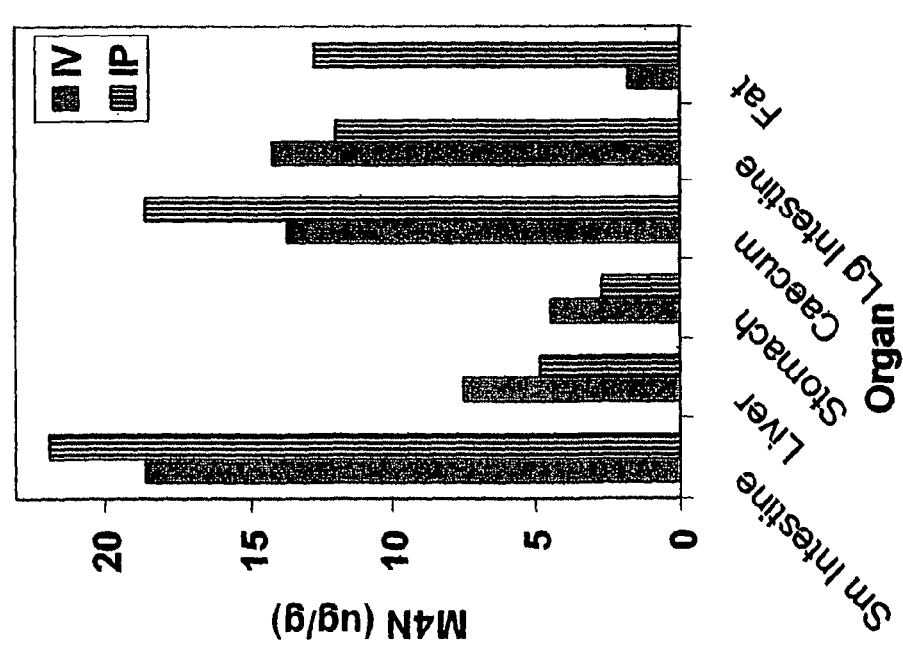

Table 1. Oral administration of $M_4N$ results in systemic tissue distribution. (A) Short-term oral feeding of $M_4N$. Three mice were fed 30 mg of $M_4N$ dissolved in castor oil. At 2, 4, and 8 hours post-feeding, tissues were removed and weighed. The quantity of $M_4N$ present in tissues was then quantitated by HPLC. (B) Long-term oral feeding of $M_4N$. Mice were continually fed food balls weighing 9 g and containing 280 mg of $M_4N$ for 14 weeks. On average, mice consumed 93.3 mg of $M_4N$ per day. The quantity of $M_4N$ present in tissues was quantitated by HPLC.

Table 2. Systemic treatment with $M_4N$ inhibits the in vivo growth of human tumor xenografts. Athymic nude mice were implanted s.c. in each flank with MCF-7 breast adenocarcinoma cells, Hep3B hepatocellular carcinoma cells, HT-29 colorectal carcinoma cells, and LNCaP prostate carcinoma cells. When tumors attained a mean diameter of 7-8 mm, mice received for three weeks a single daily i.p. injection containing 2 mg of $M_4N$ dissolved in 100 μL Cremaphor-ethanol based solvent. Control mice received vehicle only. Tumors were measured in two perpendicular dimensions (L and W) once every seven days, and tumor volumes were calculated according to the formula: $V=(L\times W/2)^3 \times \pi/6$.

Table 3. Tumor size change for all tumors following 21 days of treatment. Athymic nude mice were implanted s.c. in each flank with MCF-7 breast adenocarcinoma cells, Hep3B hepatocellular carcinoma cells, HT-29 colorectal carcinoma cells, and LNCaP prostate carcinoma cells. When tumors attained a mean diameter of 7-8 mm, mice received for three weeks a single daily i.p. injection containing 2 mg of $M_4N$ dissolved in 100 μL Cremaphor-ethanol based solvent. Control mice received vehicle only. Tumors were measured in two perpendicular dimensions (L and W) once every seven days, and tumor volumes were calculated according to the formula: $V=(L\times W/2)^3 \times \pi/6$.

DETAILED DESCRIPTION OF THE INVENTION

The inventors herein have discovered that catecholic butanes of the formula I:

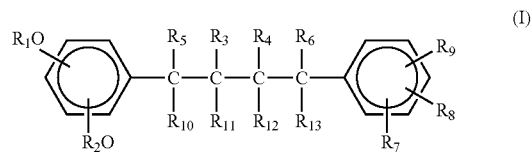

where $R_1$ and $R_2$ are independently —H, a lower alkyl, a lower acyl, an alkylene or an unsubstituted or substituted amino acid residue or salt thereof; $R_3$, $R_4$, $R_5$, $R_6$, $R_{10}$, $R_{11}$, $R_{12}$ and $R_{13}$ are independently —H or a lower alkyl; and $R_7$, $R_8$ and $R_9$ are independently —H, —OH, a lower alkoxy, a lower acyloxy, or any two adjacent groups together may be an alkyene dioxy, or an unsubstituted or substituted amino acid residue or salt thereof are useful for the treatment of proliferative diseases such as cancer, when applied other than by direct injection into the tumor or topically onto the situs of the tumor. Such catecholic butanes can be combined with pharmaceutically acceptable carrier or excipient to produce pharmaceutical compositions that can be formulated for different routes of delivery.

In another embodiment of the invention, the catecholic butane has the formula above where $R_1$ and $R_2$ are independently —H, a lower alkyl, a lower acyl, or an unsubstituted or substituted amino acid residue or salt thereof; $R_3$, $R_4$, are independently a lower alkyl; $R_5$, $R_6$, $R_{10}$, $R_{11}$, $R_{12}$ and $R_{13}$ are independently —H; and $R_7$, $R_8$ and $R_9$ are independently —H, —OH, a lower alkoxy, a lower acyloxy, or an unsubstituted or substituted amino acid residue or salt thereof.

In a further embodiment of the invention, the pharmaceutical composition has the above formula where $R_1$ and $R_2$ are independently —H, a lower alkyl, a lower acyl, or an unsubstituted or substituted amino acid residue or salt thereof; $R_3$, $R_4$, are independently a lower alkyl; $R_5$, $R_6$, $R_7$, $R_{10}$, $R_{11}$, $R_{12}$ and $R_{13}$ are independently —H; and $R_8$ and $R_9$ are independently —OH, a lower alkoxy, lower acyloxy, or an unsubstituted or substituted amino acid residue or salt thereof.

In a further embodiment of the invention, the pharmaceutical composition has the formula above where $R_1$ and $R_2$ are independently —CH$_3$ or —(C=O)CH$_2$N(CH$_3$)$_2$ or a salt thereof.

In another embodiment of the invention, the pharmaceutical composition has the formula above where $R_8$ and $R_9$ are independently —OCH$_3$ or —O(C=O)CH$_2$N(CH$_3$)$_2$ or a salt thereof.

In a further embodiment of the invention, the pharmaceutical composition has the formula above where $R_1$ and $R_2$ are independently —CH$_3$, —(C=O)CH$_2$N(CH$_3$)$_2$ or —(C=O)CH$_2$N$^+$H(CH$_3$)$_2$.Cl$^-$ and $R_8$ and $R_9$ are independently —OCH$_3$, —O(C=O)CH$_2$N(CH$_3$)$_2$ or —O(C=O)CH$_2$N$^+$H(CH$_3$)$_2$.Cl$^-$.

In yet another embodiment of the invention, the pharmaceutical composition has the formula above where $R_1$ and $R_2$ are independently —H or —CH$_3$ and $R_8$ and $R_9$ are independently —OH or —OCH$_3$, provided that the catecholic butane is not NDGA.

In a different embodiment of the invention, the pharmaceutical composition has the formula as above where $R_1$ and $R_2$ are independently —CH$_3$ and $R_8$ and $R_9$ are independently —OCH$_3$.

In yet another embodiment of the invention, the catecholic butane is NDGA. In an alternative embodiment, the catecholic butane is other than NDGA, namely, a NDGA derivative with the following formula II:

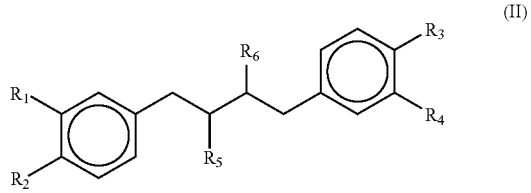

(II)

The present inventors have surprisingly discovered that a composition containing a substantially pure preparation of at least one NDGA derivative is effective for the treatment of proliferative diseases such as tumors, when such composition is administered via a route other than the direct injection into the affected or target tissues, and other than by topical application onto the affected tissue. The NDGA derivatives herein have a formula II as set forth above, where $R_1$, $R_2$, $R_3$ and $R_4$ independently represent —OH, a lower alkoxy, for example, —OCH$_3$, a lower acyloxy, for example, —O(C=O)CH$_3$, or unsubstituted or substituted amino acid residue or salt thereof but are not each —OH simultaneously; and $R_5$, $R_6$ independently represent —H or an alkyl such as a lower alkyl, for example, —CH$_3$ or —CH$_2$CH$_3$. In one embodiment, $R_5$ and $R_6$ can both be —H, —CH$_3$ or —CH$_2$CH$_3$.

The present catecholic butane, including the NDGA Compounds, in a suitable formulation, can be safely administered to one or more subjects in need of such treatment by intranasal delivery. Optionally, such catecholic butanes or NDGA Compounds can be administered by inhalation. Further optionally, such catecholic butanes or NDGA Compounds can be administered orally, such as by mixing with food, for example, or buccally, or intraocularly. Additionally, the catecholic butanes or NDGA Compounds can be administered as an oral rinse, for example, in a rinse-and-spit treatment one or more times a day.

Moreover, the catecholic butanes or NDGA Compounds formulated in liposomal formulations, nanoparticle formulations, or micellar formulations can additionally be safely administered systemically, such as intravenously, such as by injection into the central vein for example, or intraperitoneally, interstitially, subcutaneously, transdermally, intramuscularly, intra-arterially, intra-cranially, or intra-ventricularly.

Furthermore, the catecholic butanes or NDGA Compounds can be formulated in liposomal formulations, nanoparticles formulations, or micellar formulations, or any formulation embedded in a biodegradable polymer, for administration into a subject, such as one in need of such treatment. Implantation into the brain, for example, can be used for treatment of brain tumors.

In one embodiment of the invention, the route of administration for purposes herein is other than by parenteral administration, where parenteral administration herein means intravenous, intra-arterial, intramuscular, subcutaneous, transdermal and intraperitoneal administration.

The present invention further features a pharmaceutical composition containing catecholic butanes or NDGA Compounds for treatment of proliferative diseases such as tumors where the composition is formulated for delivery or administration as described above such as, for example, in the form of a tablet, a liquid that is either hydrophilic or hydrophobic, a powder such as one resulting from lyophilization, an aerosol, or in the form of an aqueous water soluble composition, a hydrophobic composition, a liposomal composition, a micellar composition, such as that based on Tween 80 or diblock copolymers, a nanoparticle composition, a polymer composition, a cyclodextrin complex composition, emulsions, lipid based nanoparticles termed "lipocores."

The present invention further features a method of producing the pharmaceutical composition of the present invention, the method involving making or providing the catecholic butanes or NDGA Compounds in a substantially purified form, combining the composition with a pharmaceutically acceptable carrier or excipient, and formulating the composition in a manner that is compatible with the mode of desired administration.

In a further aspect of the present invention, there is provided a method of treating tumor as above, where the tumor is selected from the group consisting of lung, prostate, breast, colon, liver, kidney, ovarian, cervical, skin, pancreas, brain, leukemias, lymphomas, gastrointestinal tumor such as stomach, soft tissue sarcomas and the like.

The present invention still additionally provides for kits comprising compositions or formulations as above for the treatment of proliferative diseases such as tumors where the compositions are formulated for delivery as above, including but not limited to intranasal administration, inhalation, oral administration, intravenous administration, intraperitoneal administration and other parenteral administration, or as an oral rinse, or the like, and instructions for such administration.

Definitions

Unless defined otherwise, all technical and scientific terms used herein have the same meaning as commonly understood by one of ordinary skill in the art to which this invention belongs. The present invention may be better understood in light of the particular meanings as follows.

The term "active agent," "compound," and "drug" herein refers to one or more catecholic butanes, including NDGA and NDGA derivatives.

The term "alkylene dioxy" as used herein refers to methylene (or substituted methylene) dioxy or ethylene (or substituted ethylene) dioxy.

The term "unsubstituted or substituted amino acid residue or salt thereof" in reference to one of the R groups in the formula for the catecholic butane herein is an amino acid residue or a substituted amino acid residue or salt of an amino acid residue or salt of a substituted amino acid residue including but not limited to: alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ε-N-methyllysine, ε-N,N,N-trimethyllysine, aminoadipic acid, γ-caroxyglutamic acid, phosphoserine, phosphothreonine, phosphotyrosine, N-methylarginine, N-acetyllysine, and an N,N-dimethyl-substituted amino acid residue; or a salt thereof, such as a chloride salt.

The term "lower alkyl" means $C_1$-$C_6$ alkyl.

The term "lower acyl" means $C_1$-$C_6$ acyl.

The term "NDGA Compound" refers to NDGA and/or its derivatives, singly or collectively.

The term "NDGA derivative" refers to a derivative of NDGA each having the formula II:

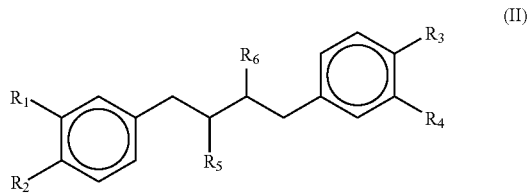

(II)

wherein $R_1$, $R_2$, $R_3$ and $R_4$ are independently —OH, lower alkoxy, lower acyloxy, or an unsubstituted or substituted amino acid residue or salt thereof but are not each —OH simultaneously; and $R_5$, $R_6$ are independently —H or an alkyl such as a lower alkyl. The term includes, for example, a compound in which $R_1$, $R_2$, $R_3$ and $R_4$ are each —OCH$_3$, or are each —O(C=O)CH$_3$; and $R_5$, $R_6$ are each —H or each a lower alkyl. In one embodiment of the invention, $R_5$, $R_6$ are each —CH$_3$ or —CH$_2$CH$_3$.

A "substantially purified" compound in reference to the catecholic butanes or NDGA Compounds herein is one that is substantially free of compounds that are not the catecholic butane or NDGA Compounds of the present invention (hereafter, "non-NDGA materials"). By substantially free is meant at least 50%, preferably at least 70%, more preferably at least 80%, and even more preferably at least 90% free of non-NDGA materials.

The "buffer" suitable for use herein includes any buffer conventional in the art, such as, for example, Tris, phosphate, imidazole, and bicarbonate.

As used herein, the terms "treatment," "treating," and the like, refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in a mammal, particularly in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. For example, the carrier for a formulation containing the present catecholic butane or NDGA Compounds preferably does not include oxidizing agents and other compounds that are known to be deleterious to such. Suitable carriers include, but are not limited to, water, dextrose, glycerol, saline, ethanol, buffer, dimethyl sulfoxide, Cremaphor EL, and combinations thereof. The carrier may contain additional agents such as wetting or emulsifying agents, or pH buffering agents. Other materials such as anti-oxidants, humectants, viscosity stabilizers, and similar agents may be added as necessary.

Pharmaceutically acceptable salts herein include the acid addition salts (formed with the free amino groups of the polypeptide) and which are formed with inorganic acids such as, for example, hydrochloric or phosphoric acids, or such organic acids as acetic, mandelic, oxalic, and tartaric. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, and histidine.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The terms "subject," "host," and "patient," are used interchangeably herein to refer to an animal being treated with the present compositions, including, but not limited to, simians, humans, felines, canines, equines, bovines, porcines, ovines, caprines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein, including patents, patent applications, and journal articles are incorporated herein by reference in their entireties including the references cited therein, which are also incorporated herein by reference.

It must be noted that as used herein, the singular forms "a", "an", and "the" include plural referents unless the context clearly dictates otherwise. Thus, for example, reference to "a compound" includes a plurality of such compounds and reference to "the NDGA Compound" includes reference to one or more NDGA Compounds and equivalents thereof known to those skilled in the art.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention described below is given by way of example only and is not to be interpreted in any way as limiting the invention.

Preparation of Catecholic Butanes

The catecholic butanes of the present invention can be prepared by any conventional methodologies. For example, such compounds can be made as described in U.S. Pat. No. 5,008,294.

Preparation of the NDGA Compounds

The NDGA Compounds and formulations thereof can be made by any process conventional in the art. For example, the NDGA Compounds can be made as described in, U.S. Pat. No. 5,008,294 (Jordan et al., issued Apr. 16, 1991); U.S. Pat. No. 6,291,524 (Huang et al., issued Sep. 18, 2001); Hwu, J. R. et al. (1998); or McDonald, R. W. et al. (2001).

In one embodiment of the present invention, an NDGA Compound, tetra-O-methyl NDGA, also known as meso-1,4-bis(3,4-dimethoxyphenyl)-2,3-dimethylbutane, or $M_4N$ is made as follows: a solution is made containing NDGA and potassium hydroxide in methanol in a reaction flask. Dimethyl sulfate is then added to the reaction flask and the reaction is allowed to proceed. The reaction is finally quenched with water, causing the product to precipitate. The precipitate is isolated by filtration and dried in a vacuum oven. The compound is then dissolved in a solution of methylene chloride and toluene and subsequently purified through an alumina column. The solvents are removed by rotary evaporation and the solid is resuspended in isopropanol and isolated by filtration. The filter cake is dried in a vacuum oven. The resulting tetra-O-methyl NDGA ($M_4N$) is crystallized by refluxing the filter cake in isopropanol and re-isolating the crystals by filtration.

In some embodiments of the present invention, certain NDGA Compounds of the present invention, such as $G_4N$, also known as meso-1,4-bis[3,4-(dimethylaminoacetoxy)phenyl]-(2R,3S)-dimethylbutane or tetra-dimethylglycinyl NDGA, or a hydrochloride salt thereof and similar compounds having amino acid substituents, can also be prepared according to conventional methods, as described in, for example, U.S. Pat. No. 6,417,234.

Compositions

The present invention further provides compositions, including pharmaceutical compositions, comprising the catecholic butanes including the NDGA Compounds and pharmaceutically acceptable carriers or excipients. These compositions may include a buffer, which is selected according to the desired use of the catecholic butanes or NDGA Compounds, and may also include other substances appropriate for the intended use. Those skilled in the art can readily select an appropriate buffer, a wide variety of which are known in the art, suitable for an intended use. In some instances, the composition can comprise a pharmaceutically acceptable excipient, a variety of which are known in the art. Pharmaceutically acceptable excipients suitable for use herein are described in a variety of publications, including, for example, A. Gennaro (1995); Ansel, H. C. et al. (1999); and Kibbe, A. H. (2000).

The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art.

Compositions for administration herein may form solutions, suspensions, tablets, pills, capsules, sustained release formulations or powders.

Therapeutic Methods

The catecholic butanes, including the NDGA Compound compositions of the subject invention find use as therapeutic agents in situations where one wishes to provide a treatment to a subject who has a proliferative disease such as a malignant, premalignant or benign tumor and where one wishes to provide treatment to viral diseases such as HIV, HPV or HSV.

A variety of animal hosts are treatable according to the subject methods, including human and non-human animals. Generally such hosts are "mammals" or "mammalian," where these terms are used broadly to describe organisms which are within the class mammalia, including the orders carnivore (e.g., dogs and cats), rodentia (e.g., guinea pigs, and rats), and other mammals, including cattle, goats, horses, sheep, rabbits, pigs, and primates (e.g., humans, chimpanzees, and monkeys). In many embodiments, the hosts will be humans. Animal models are of interest for experimental investigations, such as providing a model for treatment of human disease. Further, the present invention is applicable to veterinary care as well.

Moreover, the compounds of the present invention can be used to treat a variety of tumors and cancers, including, without limitation, acute lymphoblastic leukemia, acute myeloid leukemia, adrenocortical carcinoma, anal cancer, astrocytoma, bile duct cancer, bladder cancer, bone cancer osteosarcoma/malignant fibrous histiocytoma, brain stem glioma, brain tumor ependymoma, brain tumor medulloblastoma, breast cancer, carcinoid tumor gastrointestinal, carcinoma adrenocortical, carcinoma islet cell, cervical cancer, chronic lymphocytic leukemia, chronic myelogenous leukemia, clear cell sarcoma of tendon sheaths, colon cancer, cutaneous T-cell lymphoma, endometrial cancer, epithelial cancer ovarian, esophageal cancer, Ewing's family of tumors, extragonadal germ cell tumor, extrahepatic bile duct cancer, eye cancer, intraocular melanoma, eye cancer retinoblastoma, gallbladder cancer, gastric (stomach) cancer, gastrointestinal carcinoid tumor, germ cell tumor extragonadal, germ cell tumor, ovarian tumor, gestational trophoblastic tumor, glioma, hairy cell leukemia, hepatocellular (liver) cancer, Hodgkin's lymphoma, hypopharyngeal cancer, intraocular melanoma, islet cell carcinoma (endocrine pancreas), Kaposi's sarcoma, laryngeal cancer, leukemia acute lymphoblastic cancer, leukemia acute myeloid cancer, leukemia chronic lymphocytic cancer, leukemia chronic myelogenous cancer, leukemia hairy cell cancer, liver cancer, lung cancer non-small cell, lung cancer small cell, male breast cancer, malignant mesothelioma, medulloblastoma, melanoma, merkel cell carcinoma, multiple endocrine neoplasia syndrome, mycosis fungoides, myeloma multiple, nasal cavity, paranasal and sinus cancer, nasopharyngeal cancer, neuroblastoma, oral cavity and lip cancer, oropharyngeal cancer, osteosarcoma/malignant fibrous histiocytoma of bone, ovarian epithelial cancer, ovarian germ cell tumor, pancreatic cancer, parathyroid cancer, penile cancer, pheochromocytoma, pineal and supratentorial primitive neuroectodermal tumors, pituitary tumor, pleuropulmonary blastoma, prostate cancer, rectal cancer, renal, pelvis and ureter transitional cell cancer, retinoblastoma, rhabdomyosarcoma, salivary gland cancer, sarcoma soft tissue adult, Sezary syndrome, skin cancer, small intestine cancer, stomach (gastric) cancer, testicular cancer, thymoma, thyroid cancer, urethral cancer, uterine cancer endometrial, vaginal cancer, vulvar cancer, Waldenstrom's macroglobulinemia, and Wilms' tumor.

Formulations, Dosages, and Routes of Administration

As mentioned above, an effective amount of the active agent is administered to the host, where "effective amount" means a dosage sufficient to produce a desired result. In some embodiments, the desired result is at least a reduction or inhibition of tumor growth as compared to a control.

Typically, the compositions of the instant invention will contain from less than about 1% up to about 99% of the active ingredient, that is, the catecholic butanes including the NDGA Compounds herein; optionally, the instant invention will contain about 5% to about 90% of the active ingredient. The appropriate dose to be administered depends on the subject to be treated, such as the general health of the subject, the age of the subject, the state of the disease or condition, the weight of the subject, the size of the tumor, for example. Generally, between about 0.1 mg and about 500 mg or less may be administered to a child and between about 0.1 mg and about 5 grams or less may be administered to an adult. The active agent can be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

The frequency of administration of the active agent, as with the doses, will be determined by the care giver based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

The catecholic butanes or active agents of the present invention can be incorporated into a variety of formulations for therapeutic administration. More particularly, the catecholic butanes of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, aerosols, liposomes, nanoparticles, granules, ointments, solutions, suppositories, injections, inhalants and aerosols.

As such, administration of the active agents can be achieved in various ways, such as oral, buccal, rectal, intranasal, intravenous, intra-arterial, intra-tracheal, intraventricular, intracranial, interstitial, transdermal, etc., or by inhalation or implantation.

In particular, nanoparticle, micelle and liposomal preparation can be administered systemically, including parenterally and intranasally, as well as interstitially, orally, topically, transdermally, via inhalation or implantation, such as for drug targeting, enhancement of drug bioavailability and protection of drug bioactivity and stability. Nanoparticle bound drugs herein are expected to achieve prolonged drug retention in tumors.

In pharmaceutical dosage forms, the active agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the active agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art, such as described in, for example, Epstein, J. B. et al. (2002) and Pitten, F. et al. (2003).

The pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The active agents can be utilized in aerosol formulation to be administered via inhalation.

The compounds of the present invention can be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Kits with multiple or unit doses of the active agent, are included in the present invention. In such kits, in addition to the containers containing the multiple or unit doses of the compositions containing the NDGA derivatives will be an informational package insert with instructions describing the use and attendant benefits of the drugs in treating pathological condition of interest.

Tumors which may be treated using the methods of the instant invention include carcinomas, e.g. colon, rectum, prostate, breast, melanoma, ductal, endometrial, stomach, pancreatic, mesothelioma, dysplastic oral mucosa, invasive oral tumor, non-small cell lung carcinoma ("NSCL"), transitional and squamous cell urinary carcinoma, etc.; neurological malignancies, e.g. neuroblastoma, glioblastoma, astrocytoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; gynecological tumors, e.g., cervical and ovarian; testicular tumors; liver tumors including hepatocellular carcinoma ("HCC") and tumor of the biliary duct; multiple myelomas; tumors of the esophageal tract; other lung tumors including small cell and clear cell; Hodgkin's lymphomas; sarcomas in different organs; as well as those mentioned above; and the like.

Preparation of NanoParticles ("NP")

The present invention includes formulations of catecholic butanes, including NDGA Compounds, in a NP preparation. A number of different NP formulations suitable for use herein can be made depending on the method of delivery. The NP formulation can differ based on the drug release profile desired, by controlling the molecular weight, the copolymer ratio, the drug loading, the microparticle size and porosity and the fabrication conditions. The NP formulations can also differ on the basis of polymers, stabilizers, and surfactants used in the production process. Different excipients may also have different effects on drug uptake, drug distribution throughout the body and persistence of the drug in plasma. A person having skills conventional in the art will be able to determine the desired properties or characteristics, and accordingly determine the appropriate NP formulation to use.

The polymeric matrix of the NP must meet the criteria of biocompatibility, bioavailability, mechanical strength and ease of processing. The best known polymers for this purpose is the biodegradable poly(lactide-co-glycolide)s ("PLGAs").

NP herein can be made by any process conventional in the art. In one embodiment, the NP can be made as described in, for example, Lockman, P. R., et al. (2002). The types of manufacturing process include, for example, emulsion polymerization, interfacial polymerization, desolvation evaporation and solvent deposition.

In the emulsion polymerization process of making the NP herein, the polymerization process consists of building a chain of polymers from a single monomer unit, as described in, for example, Kreuter, J. (1994). Polymerization occurs spontaneously at room temperature after initiation by either free radical or ion formation, such as by use of high-energy radiation, UV light, or hydroxyl ions. Once polymerization is complete the solution is filtered and neutralized. The polymers form micelles and droplets consisting of from about 100 to $10^7$ polymer molecules. Surfactants and stabilizers are generally not need in this process. Also, this process can be accomplished in an organic phase rather than an aqueous phase.

The NP herein can also be made by an interfacial polymerization process as described in, for example, Khouri, A. I., et al. (1986). In this process, monomers are used to create the polymer and polymerization occurs when an aqueous and organic phase are brought together by homogenization, emulsification, or micro-fluidization under high-torque mechanical stirring. For example, polyalkylcyanoacrylate nanocapsules containing the catecholic butanes, such as the NDGA Compounds, can be made by combining the lipophilic NDGA Compounds and the monomer in an organic phase, dissolving the combination in oil, and slowly adding the mixture through a small tube to an aqueous phase with constant stirring. The monomer can then spontaneously form 200-300 nm capsules by anionic polymerization. A variation of this process involves adding a solvent mixture of benzyl benzoate, acetone, and phospholipids to the organic phase containing the monomer and the drug, as described in, for example, Fessi, H., et al. (1989). This creates a formulation in which the drug is encapsulated and protected against degradation until it reaches the target tissue.

Macromolecules such as albumin and gelatin can be used in oil denaturation and desolvation processes in the production of NPs. In the oil emulsion denaturation process, large macromolecules are trapped in an organic phase by homogenization. Once trapped, the macromolecule is slowly introduced to an aqueous phase undergoing constant stirring. The nanoparticles formed by the introduction of the two immiscible phases can then be hardened by crosslinking, such as with an aldehyde or by heat denaturation.

Alternatively, macromolecules can form NPs by "desolvation." In the desolvation process, macromolecules are dissolved in a solvent in which the macromolecules reside in a swollen, coiled configuration. The swollen macromolecule is then induced to coil tightly by changing the environment, such as pH, charge, or by use of a desolvating agent such as ethanol. The macromolecule may then be fixed and hardened by crosslinking to an aldehyde. The NDGA Compounds can be adsorbed or bound to the macromolecule before crosslinking such that the derivatives become entrapped in the newly formed particle.

Solid lipid NP can be created by high-pressure homogenization. Solid lipid NPs have the advantage that they can be sterilized and autoclaved and possess a solid matrix that provides a controlled release.

The present invention further includes NP with different methods of drug loading. The NP can be solid colloidal NP with homogeneous dispersion of the drug therein. The NP can be solid NP with the drug associated on the exterior of the NP, such as by adsorption. The NP can be a nanocapsule with the drug entrapped therein. The NP can further be solid colloidal NP with homogeneous dispersion of the drug therein together with a cell surface ligand for targeting delivery to the appropriate tissue.

The size of the NPs may be relevant to their effectiveness for a given mode of delivery. The NPs typically ranges from about 10 nm to about 1000 nm; optionally, the NPs can range from about 30 to about 800 nm; further typically, from about 60 to about 270 nm; even further typically, from about 80 to about 260 nm; or from about 90 to about 230 nm, or from about 100 to about 195. Several factors influence the size of the NPs, all of which can be adjusted by a person of ordinary skill in the art, such as, for example, pH of the solution used during polymerization, amount of initiation triggers (such as heat or radiation, etc.) and the concentration of the monomer unit. Sizing of the NPs can be performed by photon correlation spectroscopy using light scattering.

The NPs herein, such as polysaccharide NPs or albumin NPs, may optionally be coated with a lipid coating. For example, polysaccharide NPs can be crosslinked with phosphate (anionic) and quarternary ammonium (cationic) ligands, with or without a lipid bilayer, such as one containing dipalmitoyl phosphatidyl choline and cholesterol coating. Other polymer/stabilizer include, but is not limited to: soybean oil; maltodextrin; polybutylcyanoacrylate; butylcayanoacrylate/dextran 70 kDa, Polysorbate-85; polybutylcyanoacrylate/dextran 70 kDa, polysorbate-85; stearic acid; poly-methylmethylacrylate.

The NP preparations containing the catecholic butanes, such as the NDGA Compounds, such as by adsorption to the NPs, can be administered intravenously for treatment of tumors, for example, in the brain, heart and reticuloendothelial cell ("RES") containing organs, such as liver, spleen and bone marrow. To avoid undesirable uptake of these NP preparations by the reticuloendothelial cells, the NPs may be coated with a surfactant or manufactured with a magnetically responsive material.

Thus, optionally, a surfactant may be used in conjunction with the NP. For example, polybutylcyanoacrylate NPs can be used with a dextran-70,000 stabilizer and Polysorbate-80 as a surfactant. Other surfactants include, but not limited to: Polysorbate-20, 40, or 60; Poloxamer 188; lipid coating-dipalmitoyl phosphatidylcholine; Epikuron 200; Poloxamer 338; Polaxamine 908; Polaxamer 407. For example, Polyaxamine 908 may be used as a surfactant to decrease uptake of NPs into the RES of the liver, spleen, lungs, and bone marrow.

The magnetically responsive material can be magnetite ($Fe_3O_4$) which can be incorporated into the composition for making the NP. These magnetically responsive NPs can be externally guided by a magnet.

In another embodiment, the NPs herein can be made as described in Mu, L. and Feng, S. S. (2003), using a blend of poly(lactide-co-glycolide)s ("PLGAs") and d-α-tocopheryl polyethylene glycol 1000 succinate (vitamin E TPGS or TPGS). The latter can also act as an emulsifier, in addition to being a matrix material.

Preparation of Micelle Forming Carriers

The present invention includes catecholic butanes, including the NDGA Compounds, formulated in micelle forming carriers, where the micelles are produced by processes conventional in the art. Examples of such are described in, for example, Liggins, R. T. and Burt, H. M. (2002); Zhang, X. et al. (1996); and Churchill, J. R. and Hutchinson, F. G. (1988). In one such method, polyether-polyester block copolymers, which are amphipathic polymers having hydrophilic (polyether) and hydrophobic (polyester) segments, are used as micelle forming carriers.

Another type of micelles is, for example, that formed by the AB-type block copolymers having both hydrophilic and hydrophobic segments, which are known to form micellar structures in aqueous media due to their amphiphilic character, as described in, for example, Tuzar, Z. and Kratochvil, P. (1976); and Wilhelm, M. et al. (1991). These polymeric micelles are able to maintain satisfactory aqueous stability irrespective of the high content of hydrophobic drug incorporated within the micelle inner core. These micelles, in the range of approximately <200 nm in size, are effective in reducing non-selective RES scavenging and shows enhanced permeability and retention at solid tumor sites. This characteristic allows for the accumulation of anti-cancer drug, such as the NDGA derivatives, to accumulate at the cancer site.

Further, for example, poly(D,L-lactide)-b-methoxypolyethylene glycol (MePEG:PDLLA) diblock copolymers can be made using MePEG 1900 and 5000. The reaction can be allowed to proceed for 3 hr at 160° C., using stannous octoate (0.25%) as a catalyst. However, a temperature as low as 130° C. can be used if the reaction is allowed to proceed for about 6 hr, or a temperature as hight as 190° C. can be used if the reaction is carried out for only about 2 hr.

In one embodiment, N-isopropylacrylamide ("IPAAm") (Kohjin, Tokyo, Japan) and dimethylacrylamide ("DMAAm") (Wako Pure Chemicals, Tokyo, Japan) can be used to make hydroxyl-terminated poly(IPAAm-co-DMAAm) in a radical polymerization process, using the method of Kohori, F. et al. (1998). The obtained copolymer can be dissolved in cold water and filtered through two ultrafiltration membranes with a 10,000 and 20,000 molecular weight cut-off. The polymer solution is first filtered through a 20,000 molecular weight cut-off membrane. Then the filtrate was filtered again through a 10,000 molecular weight cut-off membrane. Three molecular weight fractions can be obtained as a result, a low molecular weight, a middle molecular weight, and a high molecular weight fraction. A block copolymer can then be synthesized by a ring opening polymerization of D,L-lactide from the terminal hydroxyl group of the poly(IPAAm-co-DMAAm) of the middle molecular weight fraction. The resulting poly(IPAAm-co-DMAAm)-b-poly(D,L-lactide) copolymer can be purified as described in Kohori, F., et al. (1999).

The catecholic butanes, such as the NDGA Compounds, can be loaded into the inner cores of micelles and the micelles prepared simultaneously by a dialysis method. For example, a chloride salt of the NDGA Compounds can be dissolved in N,N-dimethylacetamide ("DMAC") and added by triethylamine ("TEA"). The poly(IPAAm-co-DMAAm)-b-poly(D, L-lactide) block copolymer can be dissolved in DMAC, and distilled water can be added. The solution of NDGA Compounds and the block copolymer solution can be mixed at room temperature, followed by dialysis against distilled water using a dialysis membrane with 12,000-14,000 molecular weight cut-off (Spectra/Por®2, spectrum Medical Indus., CA. U.S.A.) at 25° C. Poly(IPAAm-co-DMAAm)-b-poly(D,L-lactide) micelles incorporating NDGA Compounds can be purified by filtration with a 20 nm pore sized microfiltration membrane (ANODISC™, Whatman International), as described in Kohori, F., et al. (1999).

Preparation of Multivesicular Liposomes Containing NDGA Compounds

Multivesicular liposomes ("MVL") can be produced by any method conventional in the art, such as, for example, the double emulsification process as described in Mantripragada, S. (2002). Briefly, in the double emulsification process, a "water-in-oil" emulsion is first made by dissolving amphipathic lipids, such as a phospholipid containing at least one neutral lipid, such as a triglyceride, in one or more volatile organic solvents, and adding to this lipid component an immiscible first aqueous component and a hydophobic catecholic butane, such as a hydrophobic NDGA Compound. The mixture is then emulsified to form a water-in-oil emulsion, and then mixed with a second immiscible aqueous component followed by mechanical mixing to form solvent spherules suspended in the second aqueous component, forming a water-in-oil-in-water emulsion. The solvent spherules will contain multiple aqueous droplets with the catecholic butane, such as the NDGA Compound dissolved in them. The organic solvent is then removed from the spherules, generally by evaporation, by reduced pressure or by passing a stream of gas over or through the suspension. When the solvent is completely removed, the spherules become MVL, such as DepoFoam particles. When the neutral lipid is omitted in this process, the conventional multilamellar vesicles or unilamellar vesicles will be formed instead of the MVL.

Formulation of Catecholic Butanes, such as NDGA Compounds for Oral Delivery

Some catecholic butanes, such as NDGA Compounds are water-soluble, hydrophilic compounds, such as $G_4N$. This invention includes formulation of hydrophilic compounds in a pharmaceutically acceptable carrier or excipient and delivery of such as oral formulations, such as in the form of an aqueous liquid solution of the compound, or the compounds can be lyophilized and delivered as a powder, or made into a tablet, or the compounds can be encapsulated.

The tablets herein can be enteric coated tablets. The formulations herein can be sustained release, either slow release or rapid release formulations.

The amount of the catecholic butanes, such as NDGA Compounds, to be included in the oral formulations can be adjusted depending on the desired dose to be administered to a subject. Such an adjustment is within the skill of persons conventional in the art.

Some catecholic butanes, including some NDGA Compounds, are hydrophobic or lipophilic compounds, such as $M_4N$. The absorption of lipophilic compounds in the gut can be improved by using pharmaceutically acceptable carriers that can enhance the rate or extent of solubilization of the compound into the aqueous intestinal fluid. Lipidic carriers are known in the art, such as, for example, as described in Stuchlik, M. and Zak, S. (2001) The formulations herein can be delivered as oral liquids or can be encapsulated into various types of capsules.

The present invention includes, in one embodiment, a formulation containing the lipophilic NDGA Compounds that are formulated for oral delivery by dissolution of such compounds in triacylglycerols, and the formulation is then encapsulated for oral delivery. Triacyglycerols are molecules with long chain and/or medium chain fatty acids linked to a glycerol molecule. The long chain fatty acids range from about $C_{14}$ to $C_{24}$, and can be found in common fat. The medium chain fatty acids range from about $C_6$ to $C_{12}$, and can be found in coconut oil or palm kernel oil. Triacylglycerols suitable for use herein include structured lipids that contain mixtures of either short-chain or medium chain fatty acids or both, esterified on the same glycerol molecule.

In another embodiment of the present invention, one or more surfactants can be added to a mixture of catecholic butanes, including NDGA Compounds, and lipidic carrier such that the drug is present in fine droplets of oil/surfactant mix. The surfactants can act to disperse the oily formulation on dilution in the gastrointestinal fluid.

The present invention also includes a formulation for oral delivery of the catecholic butanes, including NDGA Compounds, in the form of a micro-emulsion consisting of hydrophilic surfactant and oil. The micro-emulsion particles can be surfactant micelles containing solubilized oil and drug.

Also suitable for oral administration are formulations of the catecholic butanes, including NDGA Compounds, in a solid lipid nanoparticle preparation. Solid lipid nanoparticles can be prepared in any manner conventional in the art, such as, for example, as described in Stuchlik, M. and Zak, S. (2001).

In one embodiment, the solid lipid nanoparticle can be prepared in a hot homogenization process by homogenization of melted lipids at elevated temperature. In this process, the solid lipid is melted and the catecholic butane, such as the NDGA Compound, is dissolved in the melted lipid. A preheated dispersion medium is then mixed with the drug-loaded lipid melt, and the combination is mixed with a homogenisator to form a coarse pre-emulsion. High pressure homogenization is then performed at a temperature above the lipids melting point to produce a oil/water-nanoemulsion. The nanoemulsion is cooled down to room temperature to form solid lipid nanoparticles.

In another embodiment of the present invention, the solid lipid nanoparticles can be prepared in a cold homogenization process. In this process, the lipid is melted and the catecholic butane, such as the NDGA Compound, is dissolved in the melted lipid. The drug-loaded lipid is then solidified in liquid nitrogen or dry ice. The solid drug-lipid is ground in a powder mill to form 50-100 μm particles. The lipid particles are then dispersed in cold aqueous dispersion medium and homogenized at room temperature or below to form solid lipid nanoparticles.

The present invention also includes formulation of the lipophilic catecholic butanes, such as NDGA Compounds, in liposomes or micelles for oral delivery. These formulations can be made in any manner conventional in the art. Micelles are typically lipid monolayer vesicles in which the hydrophobic drug associates with the hydrophobic regions on the monolayer. Liposomes are typically phospholipids bilayer vesicles. The lipophilic catecholic butane, such as the lipophilic NDGA Compounds, will typically reside in the center of these vesicles.

Intra-Arterial Administration

The present invention includes formulation of the catecholic butanes, as exemplified by the NDGA Compounds, for intra-arterial administration as is conventional in the art, as described in, for example, Doolittle, N. D. et al. (2000); and Cloughesy, T. F. et al. (1997), with or without accompanying blood brain barrier disruption ("BBBD"), and with or without occlusion, such as in hepatic artery chemoemobolization, as described in Drougas, J. G. et al. (1998); and Desai, D. C. et al. (2001). Briefly, where NDGA Compounds are administered intra-arterially with occlusion, primary arteries leading to the target site are catheterized and the NDGA Compounds are applied through a catheter. Embolization of the arteries, in order to retain the NDGA Compounds at the target site for a longer period, is performed using polyvinyl alcohol particles alone or in combination with coils. Intra-arterial delivery of the NDGA Compounds is limited to water soluble compositions. Water soluble NDGA Compounds, such as $G_4N$, for example, liposomal formulations of hydrophobic NDGA Compounds, such as $M_4N$, for example, or nanoparticle formulations of hydrophobic NDGA Compounds are particularly suited for this type of delivery. The drugs or agents herein can be dissolved in saline prior to intra-arterial injection and such injection may be preceded by heparin treatment and sedation. For safest treatment of brain tumor, preferably, intra-arterial administration is conducted before tumor burden becomes excessive.

Osmotic disruption of the blood brain barrier ("BBB") as conventional in the art may accompany intra-arterial delivery of the agents herein as described in, for example, Doolittle, N. D. et al. (2000); Sato, S. et al., Acta Neurochir (Wien) 140: 1135-1141; disc 1141-1132 (1998); and Bhattacharjee, A. K. et al. Brain Res Protocol 8: 126-131 (2001). Such a procedure can be used to increase the transfer of drugs into the central nervous system ("CNS") preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Formulation of NDGA Compounds for Intranasal Delivery

The present invention includes formulations of catecholic butanes, as exemplified by the NDGA Compounds, for intranasal delivery and intranasal delivery thereof. Intransal delivery may advantageously build up a higher concentration of the active agents in the brain than can be achieved by intravenous administration. Also, this mode of delivery avoids the problem of first pass metabolism in the liver and gut of the subject receiving the drug.

The amount of the active agents that can be absorbed partly depends on the solubility of the drug in the mucus, a composition that consists of about 95% water solution of serum proteins, glycoproteins, lipids and electrolytes. Generally, as lipophilicity of the active agents herein increases, the drug concentration in the CSF also increases. See, for example, Minn, A. et al. (2002).

The hydrophilic NDGA Compounds can be dissolved in a pharmaceutically acceptable carrier such as saline, phosphate buffer, or phosphate buffered saline. In one embodiment, a 0.05 M phosphate buffer at pH 7.4 can be used as the carrier, as described in, for example, Kao, H. D., et al. (2000).

Intranasal delivery of the present agents may be optimized by adjusting the position of the subject when administering the agents. For example, the head of the patient may be variously positioned upright-90°, supine-90°, supine-45°, or supine-70°, to obtain maximal effect.

The carrier of the composition of NDGA Compounds may be any material that is pharmaceutically acceptable and compatible with the active agents of the composition. Where the carrier is a liquid, it can be hypotonic or isotonic with nasal fluids and within the pH of about 4.5 to about 7.5. Where the carrier is in powdered form it is also within an acceptable pH range.

The carrier composition for intranasal delivery may optionally contain lipophilic substances that may enhance absorption of the active agents across the nasal membrane and into the brain via the olfactory neural pathway. Examples of such lipophilic substances include, but are not limited to, gangliosides and phosphatidylserine. One or several lipophilic adjuvants may be included in the composition, such as, in the form of micelles.

The pharmaceutical composition of active agents for intranasal delivery to a subject for treatment of tumor and other proliferative diseases, disorders, or conditions herein can be formulated in the manner conventional in the art as described in, for example, U.S. Pat. No. 6,180,603. For example, the composition herein can be formulated as a powder, granules, solution, aerosol, drops, nanoparticles, or liposomes. In addition to the active agents, the composition may contain appropriate adjuvants, buffers, preservatives, salts. Solutions such as nose drops may contain anti-oxidants, buffers, and the like.

Delivery by Implantation

The catecholic butanes herein, as exemplified by the NDGA Compounds, may be delivered to a subject for treatment by surgical implantation into a tumor site, with or without surgical excision of the tumor, such as by implantation of a biodegradable polymer containing the NDGA Compounds. In one embodiment, this method of treatment can be performed, for example, after surgical resection, such as in the treatment and resection of brain tumor, as described in, Fleming, A. B. and Saltzman, W. M., Pharmacokinetics of the Carmustine Implant, Clin. Pharmacokinet, 41: 403-419 (2002). This method of delivery is applicable to not only brain tumors but to other tumors as well. This treatment may be combined with other conventional therapy besides or in addition to surgery, such as radiotherapy, chemotherapy or immunotherapy.

Thus, the biodegradable polymer herein can be any polymer or copolymer that would dissolve in the interstitial fluid, without any toxicity or adverse effect on host tissues. Preferably, the polymer or monomers from which the polymer is synthesized is approved by the Food and Drug Administration for administration into humans. A copolymer having monomers of different dissolution properties is preferred so as to control the dynamics of degradation, such as increasing the proportion of one monomer over the other to control rate of dissolution.

In one embodiment, the polymer is a copolymer of 1,3-bis-(p-carboxyphenoxy)propane and sebacic acid [p(CPP:SA)], as described in Fleming A. B. and Saltzman, W. M., Pharmacokinetics of the Carmustine Implant, Clin. Pharmacokinet, 41: 403-419 (2002); and Brem, H. and Gabikian, P. (2001). In another embodiment, the polymer is a copolymer of polyethylene glycol ("PEG") and sebacic acid, as described in Fu, J. et al., (2002).

Polymer delivery systems are applicable to delivery of both hydrophobic and hydrophilic NDGA Compounds herein. The NDGA Compounds are combined with the biodegradable polymers and surgically implanted at the tumor site. Some polymer compositions are also usable for intravenous or inhalation therapy herein.

Delivery Through Inhalation

The catecholic butanes herein, as exemplified by the NDGA Compounds, may be delivered systemically and/or locally by administration to the lungs through inhalation. Inhalation delivery of drugs has been well accepted as a method of achieving high drug concentration in the pulmonary tissues without triggering substantial systemic toxicity, as well as a method of accomplishing systemic circulation of the drug. The techniques for producing such formulations are conventional in the art. Efficacy against pulmonary diseases may be seen with either hydrophobic or hydrophilic NDGA Compounds delivered in this manner.

For pulmonary delivery via inhalation, the NDGA Compounds herein may be formulated into dry powders, aqueous solutions, liposomes, nanoparticles, or polymers and administered, for example, as aerosols. Hydrophilic formulations may also be taken up through the alveolar surfaces and into the bloodstream for systemic applications.

In one embodiment, the polymers containing the active agents herein are made and used as described in Fu, J. et al. (2002). For example, the polymers herein can be polymers of sebacic acid and polyethylene glycol ("PEG"), or can be poly(lactic-co-glycolic) acid ("PLGA"), or polymers of polyethyleneimine ("PEI") and poly-L-lysine ("PLL").

In another embodiment, the NDGA Compounds for inhalation delivery may be dissolved in saline or ethanol before nebulization and administered, as described in Choi, W. S. et al. (2001).

In a further embodiment, the agents herein are also effective when delivered as a dry powder, prepared in the manner conventional in the art, as described in, for example, Patton, J. S. et al., Inhaled Insulin, Adv. Drug Deliv. Rev., 35: 235-247 (1999).

The present invention includes delivery of the NDGA Compounds with the aid of microprocessors embedded into drug delivery devices, such as, for example, SmartMist™ and AERx™, as described in, for example, Gonda, I., et al. (1998).

After reading the present disclosure, those skilled in the art will recognize other disease states and/or symptoms which might be treated and/or mitigated by the administration of formulations of the present invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Examples in the present tense are prophetic examples.

Example 1

Preparation of a Preparative Batch of Tetra-O-Methyl-NDGA

Tetra-O-Methyl-NDGA, referenced herein as $M_4N$, was synthesized by the reaction of NDGA with excess dimethyl sulfate in the presence of base, such as potassium hydroxide. The product was isolated by the addition of water causing precipitation of the product. The reaction product was passed through a plug of basic alumina to remove traces of phenolic impurities, primarily various species of di-O-methyl and tri-O-methyl-substituted NDGA. After the solution of the reaction mixture had passed through the alumina plug, the solvent was removed on a rotary evaporator giving a solid product. This was triturated with 2-propanol, filtered and dried in a vacuum oven to give crude tetra-O-methyl-NDGA. Crystallization from 2-propanol gave tetra-O-methyl-NDGA with a purity of greater than or equal to 99.66%.

Step 1: Synthesis of Crude Preparation of Tetra-O-Methyl-NDGA

A 22 L flask fitted with a mechanical stirrer, condenser and inlet for inert atmosphere was set up in a tub for use as a cooling bath. The flask was placed under an argon atmosphere, and was charged with 484.3 grams of NDGA (Western Engineering & Research Co, El Paso, Tex.), and 4850 mL of methanol and stirred. To the stirred slurry was added a solution of 387.5 grams of potassium hydroxide in 1210 mL of deionized water. The flask containing this reaction mixture was cooled using an ice bath, and dimethyl sulfate (1210 mL) was slowly added (dropwise). The addition was controlled to avoid an exotherm. At the end of the addition, the temperature was about 13° C. The pH of the reaction was monitored, and a 50% KOH solution was added in portions during the day to maintain a basic pH; a total of 1400 mL of 50% KOH solution was added. The reaction mixture with excess base gave a pH of about 12, as detected using pH indicating strips. The solution was dark at basic pH, but became light colored at neutral or acidic pH.

At the end of the day, an additional 600 mL of dimethyl sulfate was added, and the reaction mixture was allowed to stir overnight. The next morning, the reaction was still basic, and the reaction had progressed to about 90%.

The reaction mixture was quenched by the addition of 4850 mL of deionized water, causing the product to precipitate. The product was isolated by filtration, the filter cake washed thoroughly with water, and the product dried in a vacuum oven at 50° C. for approximately 65 hr to give 539.5 g of the crude product. This product was dissolved in 750 mL of methylene chloride, and to this solution was added 375 mL of toluene. This solution was passed through a short column of 2215 g of basic alumina. The alumina was eluted with 12,000 mL of a methylene chloride/toluene solution (2:1). Removal of the solvent in vacuo on a rotary evaporator gave a solid residue. This was triturated with 1 L of 2-propanol. The resulting slurry was filtered to isolate the solid product. This was dried in a vacuum oven at 50° C. under high vacuum for approximately 21 hr to give 426.7 g (74% yield) of crude tetra-O-methyl-NDGA.

Step 2—Crystallization of Tetra-O-Methyl-NDGA

A 3 L flask with mechanical stirrer, condenser, and inlet was placed in a heating mantle, and was charged with 415.4 g of the product. The flask was charged with 1245 mL of 2-propanol, and the stirred mixture was heated to give a mild reflux; a solution was obtained. The heat was turned off, and the mixture was allowed to cool overnight. The crystalline product was isolated by filtration, and the filter cake washed with 200 mL of cold 2-propanol. The product was dried in a vacuum oven at 50° C. under high vacuum to constant weight giving 404.7 g (70.5% yield overall from NDGA).

Example 2

Preparation of PLGA Nanoparticles Containing NDGA Compounds

The NDGA Compounds can be formulated as a nanoparticle preparation in any manner conventional in the art. For example, the nanoparticles can be prepared as described in Lamprecht, A. et al. (2001a); and Lamprecht, A. et al. (2001b) and as follows.

The biodegradable polymer poly[DL-lactide-co-glycolide] 50/50 (PLGA) (mol. wt. 5,000 or 20,000) can be purchased from Wako (Osaka, Japan). About 40 mg of a NDGA Compound can be dissolved in 4 ml of methylene chloride containing 250 mg of the polymer poly [DL-lactide-coglycolide] 50/50 (mol. wt. 5,000 or 20,000). This solution can thereafter be poured into 8 ml of aqueous polyvinyl alcohol solution (1%) and homogenized with an ultrasonifier (Ultrasonic Disruptor model UR-200P; Tomy Seiko Co., Ltd., Tokyo, Japan) in an ice bath for 3 min. The methylene chloride can be evaporated under reduced pressure, and the polymer precipitated. The nanoparticles can be separated from the non-encapsulated drug and free surfactant by centrifugation (14,000 g for 5 min). Nanoparticles can be redispersed and centrifuged three times in distilled water before lyophilization. Before oral administration, the nanoparticles can be re-dispersed in phosphate buffer at pH 6.8.

The nanoparticles can be analyzed for their size distribution and their surface potential using a Photal laser particle analyzer LPA 3100 (Otsuka Electronics, Osaka, Japan) and a Zetasizer II (Malvern Instruments, Worcestershire, U.K.) respectively. The external morphology of the nanoparticles can be analyzed with a JEOL JSM-T330A scanning microscope (Tokyo, Japan).

Example 3

Preparation of PLGa/Vitamin E TPGS Nanoparticles with NDGA Compounds

NPs containing PLGA and another matrix material, d-α-tocopheryl polyethylene glycol 1000 succinate (vitamin E TPGS or TPGS), can be made as described in Mu, L. and Feng, S. S. (2003), a modified oil-in-water single emulsion solvent evaporation/extraction method. In this method, known amounts of mass of polymer and NDGA Compounds are added into methylene chloride (dichloromethane). The polymer, for example, poly(DL-lactide-co-glycolide (PLGA; L/G=50/50, MW 40,000-75,000; L/G=75/25, MW 90,000-120,000; and L/G=85/15, MW 90,000-120,000), can be purchased from Sigma (USA). Vitamin E TPGS can be obtained from Eastman Chemical, USA. The mixture is stirred to ensure that all the materials are dissolved. The solution of organic phase is then slowly poured in the stirred aqueous solution with or without emulsifier and sonicated simultaneously at 50 W in pulse mode (Misonix, USA). The formed o/w emulsion can be gently stirred at room temperature (22° C.) by a magnetic stirrer overnight to evaporate the organic solvent. The resulting sample can be collected by centrifugation, such as at 10,000 rpm, 10 min. 16° C. (Eppendorf model 5810R, Eppendorf, Hamburg, Germany) and washed once or twice with deionized water for some samples. The produced suspension can be freezed dried (Alpha-2, Martin Christ Freeze Dryers, Germany) to obtain a fine powder of nanoparticles, which can be placed and kept in a vacuum dessicator.

Example 4

Preparation of Liposomes Containing NDGA Compounds

The NDGA Compounds, such as the lipophilic drugs, can be encapsulated in long acting liposomes by processes conventional in the art. One such method is described in, for example, Sharma, U.S. et al. (1997).

Long-acting liposomes have extended blood circulation time. They are typically composed of high phase-transition $T_m$ lipids, high cholesterol content, and a component such as phosphatidyl inositol, monosialoganglioside ($GM_1$), or synthetic phospholipids bearing a polyethylene glycol (PEG) headgroup, which provides a steric barrier against plasma protein access to the liposome surface.

In an example, liposomes composed of phosphatidylcholine ("PC"): cholesterol ("Chol"): polyethylene glycol conjugated to dipalmitoylphosphatidylethanolamine ("PEG-DPPE") in a molar ratio of 9:5:1 can be prepared. The lipids are initially mixed in chloroform, and a thin film of lipid can be produced by evaporation of the solvent. The lipids are then hydrated in a buffer consisting of NaCl (145 mM), Tris[Hydroxymethyl]-2-aminoethane-sulfonic acid (TES: 10 mM), and ethylenediamine tetraacetate (EDTA: 0.1 mM) buffer, pH 7.2. The liposomes can then be extruded several times through 0.08 µm polycarbonate filters.

In another example, liposomes composed of distearoylphosphatidylcholine ("DSPC"): Chol: PEG-DSPE in at a molar ratio of 9:5:1 can be prepared using a "remote loading" method as described in Madden, T. D., et al. (1990). This remote loading method allows for encapsulation of high concentration of NDGA Compounds within the liposome aqueous core. Briefly, a thin film of lipids can be hydrated in ammonium sulfate (250 mM, pH 5.5). The lipid suspension can be extruded through 0.08 µm polycarbonate filters at 60° C. and dialyzed overnight against isotonic sucrose to remove free ammonium sulfate. Hydrophilic NDGA Compounds can be hydrated in 10% (w/v) sucrose and incubated with the preformed liposomes for 1 hr at 65° C. The preparation can be dialyzed against isotonic sucrose to remove the minor residual fraction of unencapsulated drug. This method may yield encapsulation efficiencies of greater than or equal to 90% of the initial NDGA compounds.

Poly(lactide-co-glycolide)-monomethoxy-poly(polyethylene glycol) (PLGA-mPEG) copolymers of different molar ratios can be prepared by a melt polymerization process under vacuum using stannous octoate as catalyst, as described in Beletsi, A et al. (1999); and Avgoustakis, K. et al. (2002).

Example 5

Preparation of Intranasal Formulations of NDGA Compounds

The NDGA Compounds can be formulated as a dry powder or an aerosol for intranasal delivery by any methods conventional in the art, such as, for example, as described in Marttin, E. et al. (1997).

In one embodiment, the NDGA Compound is formulated as a solution with randomly methylated β-cyclodextrin ("RAMEB") (degree of substitution 1.8) (Wacker, Burghausen, Germany), mannitol or glucose in MQ water, water that is filtered by a Mili-Q UF plus ultrapure water system from Millipore (Etten-Leur, The Netherlands). This formulation may be administered as a spray or as drops. The dose of NDGA Compound in the liquid formulation may be from about 1 mg/ml to about 1500 mg/ml, or optionally from about 10 mg/ml to about 1200 mg/ml, or further optionally from about 100 mg/ml to about 1000 mg/ml, or still optionally, from about 200 mg/ml to about 800 mg/ml, or any value that falls between these ranges. These liquid formulations can be sprayed into the nostril or applied as drops.

In another embodiment, the present invention includes lyophilized powder formulations of NDGA Compounds, prepared by dissolving the NDGA Compounds and various amounts of RAMEB, lactose, or mannitol in MQ water, and lyophilizing the mixture, such as, for example, overnight.

Example 6

Production of a Biodegradable Polymer Implant

The NDGA Compounds herein can be incorporated into a biodegradable polymer for implantation into tumors that are not operable. Such biodegradable polymer can be made by any method conventional in the art, such as described in Fleming, A. B. and Saltzman, W. M. (2002). Typically, the polymer implant is inserted after removal of the bulk of the tumor. One or more wafers of this biodegradable polymer can be implanted at one time depending on the dose of the compounds desired. The biodegradable matrix of the polymer can be made up of polifeprosan 20, a copolymer of 1,3-bis-(p-carboxyphenoxy)propane and sebacic acid [p(CCP:SA)] in a 20:80 molar ratio. To form the polymer for implant, p(CPP:SA) and a compound herein can be co-dissolved in dichloromethane and spray dried to form spherical particles with a size range of about 1 to about 20 µm. The resulting "microspheres" are compression moulded to form wafers of any desired size, such as, for example, about 14 mm in diameter and about 1 mm in thickness. The wafers have a homogeneous structure consisting of densely packed microspheres surrounded by small gaps. Concentration of the NDGA Compounds can be in any amount appropriate for the subject to be treated, such as, for example, 3.8% active compound.

Example 7

Preparation of PLGA-mPEG Nanoparticles

PLGA-mPEG nanoparticles containing the NDGA Compounds can be prepared using the double emulsion method described by Song C. X. et al (1997), with minor modifications. Here, an aqueous solution of the NDGA Compounds can be emulsified in dichloromethane in which the copolymer is dissolved, using probe sonication (Bioblock Scientific, model 75038). This water/oil emulsion can be transferred to an aqueous solution of sodium cholate and the mixture can be probe sonicated. The resulting water/oil/water emulsion formed can be gently stirred at room temperature until evaporation of the organic phase is complete. The nanoparticles made in this way can be purified by centrifugation and reconstituted with deionized and distilled water. The nanoparticles can then be filtered such as through a 1.2-µm filter (Millex AP, Millipore).

Example 8

Preparation of Pluronic Micelles Containing NDGA Compounds

Pluronic is a triblock PEO-PPO-PEO copolymer, with PEO representing poly(ethylene oxide), and PPO representing poly(propylene oxide). The hydrophobic central PPO blocks form micelle cores, while the flanking PEO blocks form the shell or corona, which protects the micelles from recognition by the reticuloendothelial system ("RES"). Pluronic copolymers are commercially available from BASF Corp, and ICI. The NDGA Compounds can be introduced into the Pluronic micelles by any method conventional in the art, as described in, for example, Rapoport, N. Y., et al. (1999).

Briefly, the NDGA Compounds can be dissolved in PBS or RPMI medium, followed by a short, such as 15 sec, sonication in a sonication bath operating at 67 kHz. The solution can be kept for about 2 hr at 37° C., upon which the non-solubilized drug can be removed by dialysis through a 1000 D cutoff membrane at 37° C. for about 12 hr against PBS or RPMI medium (dialysis to be done only for 10 and 20 wt % Pluronic solutions).

Example 9

Administration of NDGA Compounds by Implantation

Implantation of the NDGA Compounds herein can be done in any manner conventional in the art. In one embodiment, implantation is performed as described in Brem, H., and Gabikian, P. (2001). It is preferable that prior to the insertion of the polymer implant that the tumor be surgically debulked. Further the dura should be closed in a water-tight fashion to eliminate cerebrospinal fluid leakage and to decrease risk of infection. It is also desirable to use preoperative anti-convulsants and high dose steroids as necessary for neurologic compromise. It is further desirable to continue steroid therapy for at least 2 weeks post-operatively.

Example 10

Delivery of NDGA Compounds in Ethanol Via Inhalation

The NDGA Compounds herein can be delivered via inhalation using any formulation conventional in the art, including as dry powders or as aqueous solutions. The former has the advantage of stability, low susceptibility to microbial growth and high mass per puff. Aqueous solutions offer better reproducibility and avoid the issue of clumping.

In one embodiment, certain of the NDGA Compounds are delivered according to the method as described in Choi, W. S. et al. (2001). Depending on the particular compound and the solubility thereof, the compounds can be formulated to an appropriate concentration in ethanol, such as, for example in a range of from about 1 mg/ml to about 1000 mg/ml, or any intervening values in-between, such as, for example, between about 2 mg/ml and about 800 mg/ml, or between about 4 mg/ml and about 100 mg/ml, or between about 5 mg/ml and about 50 mg/ml. Aerosol particles of 1-3 µm size can be generated for maximal deep lung delivery. For better solubility of the compounds in ethanol, the compounds herein can be first lyophilized, then acidified if necessary or desirable, such as with $H_3PO_4$. The pH of the resulting composition can be adjusted with NaOH, if desired, such as to pH 7.4. The resulting composition can then be lyophilized, suspended in ethanol, sonicated and stirred to produce appropriate submicron size particles. The aerosolized compounds can then be administered using a standard commercial nebulizer, such as a compressor (air jet) or an ultrasonic type, or a metered dose inhaler. An example is a PARI LC Jet+ nebulizer (PARI Respiratory Equipment, Monterey, Calif.) in conjunction with a PARI PRONEB compressor. A volume of about 9 ml can be charged in the reservoir of the nebulizer and nebulized for up to about 10 min.

In another embodiment, the formulation for inhalation can be prepared as described in Wang, D. L., et al. (2000). For example, powdered NDGA Compounds can be dissolved in 10:90 (v/v) polyethylene glycol 300:100% ethanol containing 0.5% (w/v) ascorbic acid and 0.5% (w/v) phosphatidylcholine. The drug formulation can then be aerosolized using a Pari LC-plus nebulizer (Pari, Richmond, Va.) and a subject to be treated can be exposed to the aerosol generated for varying lengths of time, depending on the dose of the formulation and the desired concentration to be achieved. Such periods of time can be about 5 minutes, 10 minutes, 15 minutes or longer.

Example 11

Delivery of NDGA Compounds Using Specially Designed Inhalator

The NDGA Compounds can also be formulated in a number of other pharmaceutically acceptable carriers for inhalation purposes. In this example, certain of the compounds herein can be delivered according to the method of Enk, A. H. et al. (2000). Such compounds can be dissolved in a solution containing about 5% glucose and 2% human albumin. Inhalation can then be performed using a specially designed inhalator. (Jetair, Fa. Hoyer, Germany).

Example 12

Delivery of NDGA Derivatives as an Oral Rinse for Treatment of Oral Lesions

The delivery of NDGA derivatives to the oral cavity involves the use of an oral rinse using excipients that are conventional in the art, such as, for example, that described in Armstrong W. B., et al. (2000). The NDGA derivatives are dispensed as a powder that is reconstituted in an appropriate delivery fluid, such as Roxane Saliva Substitute (Roxane Laboratories, Columbus, Ohio), immediately before use. Patients then hold the NDGA derivative suspension in the mouth for about 1 minute before expectorating or swallowing the drug mixture. This procedure is carried out at least once daily for local delivery of NDGA derivatives to the oral cavity.

Alternatively, the delivery of NDGA derivatives to the oral cavity can involve an oral rinse formulation such as described in Epstein, J. B., et al. (2001). Briefly, the NDGA derivatives are prepared in an oral rinse containing about 0.1% alcohol and sorbitol. Patients are provided with a suitable volume, such as about 5 ml of the rinse, to be rinsed in the mouth for about 1 minute and expectorated. This procedure is carried out at least once daily for local delivery of NDGA derivatives to the oral cavity.

Example 13

Arrest of Tumor Growth in Mice After Systemic or Oral Administration of $M_4N$

In this example, the inventors considerably expanded the cancer therapeutic potential of $M_4N$ by investigating both its anti-tumor efficacy in vivo against several human cancer xenograft models, and its ability to be administered systemically through various routes of administration at pharmacologically relevant levels. This example shows the following: (1) when administered in vivo through differing routes of systemic administration including intraperitoneal (IP) injection, intravenous (IV) injection, and oral feeding, $M_4N$ distributes consistently to various organs and to tumors with little or no apparent toxicity to mice; (2) systemic IP administration of $M_4N$ effectively retards the in vivo growth of xenografts from 4 human cancer cell types: MCF-7 breast adenocarcinoma, Hep3B hepatocellular carcinoma, HT-29 colorectal carcinoma, and LNCaP prostate carcinoma; and systemic oral administration of $M_4N$ effectively suppresses the growth of LNCaP xenograft tumors—only LNCaP tumors have thus far been assessed in oral administration efficacy studies.

Cell Lines and Culture Conditions. Human tumor cell lines were purchased from ATCC (Mannassas, Va.). The human hepatocellular carcinoma cell line, Hep 3B, and the human breast epithelial adenocarcinoma cell line, MCF-7, were grown in Eagle's Minimal Essential Media+10% FBS+penicillin+streptomycin. The human colorectal adenocarcinoma cell line, HT-29, was grown in McCoy's 5a Medium+10% FBS+penicillin+streptomycin. The human prostate carcinoma cell line, LNCaP was grown in RPMI 1640+10% FBS+penicillin+streptomycin.

Mice. Female ICR mice, 6-8 weeks of age, were purchased from Harlan Sprague Dawley (Indianapolis, Ind.). C57bl/6 mice were purchased from Charles River Laboratories (Wilmington, Mass.). Athymic (thy$^-$/thy$^-$) nude mice, males and females 5-6 weeks of age, were purchased from Charles River Laboratories and were housed in a pathogen-free room under controlled temperature and humidity in accordance with Institutional Animal Care and Use Guidelines. C57bl/6 mice bearing C3 cell-induced tumors were prepared as described in Kim, E. H. et al. (2004).

Xenograft Assay of Human Tumors. Athymic nude mice were implanted subcutaneously in their flanks with $2.5 \times 10^6$ Hep3B cells, $2 \times 10^6$ LNCaP cells, $1 \times 10^7$ HT-29 cells, or $2 \times 10^6$ MCF-7 cells. After the tumors exhibited a mean diameter of 7-8 mm, the mice were assigned to one of two groups: a control group receiving vehicle only, and a group receiving $M_4N$ dissolved in the Cremaphor EL-ethanol-based solvent system. Assignment was made so that both the control group and the experimental group contained mice bearing tumors of comparable sizes.

$M_4N$ was dissolved in 6% Cremaphor EL, 6% ethanol, 88% saline as described in Loganzo et al. (2003). Mice received a single daily 100 µL i.p. injection containing 2 mg of $M_4N$ for 3 weeks. The control mice received an equal volume of the vehicle. Tumors were measured in two perpendicular dimensions (L and W) once every seven days, and the tumor volumes were calculated according to the following formula: $V=(L \times W/2)^3 \times \pi/6$. The results from the individual mice were plotted as average tumor volume versus time. Statistical significance of the mean differences in tumor volume was assessed by Student's t-test. At the termination of the experiment, tumor biopsies were collected for immunohistological analysis of cdc2 and survivin expression.

$M_4N$ Tissue Distribution Studies Using $^3H$-$M_4N$. Harlan ICR mice or C3 cell-induced tumor-bearing C57bl/6 mice were injected via tail vein or intraperitoneally with 100 µL of Cremaphor-ethanol based solvent containing 100 µCi of tritiated $M_4N$ and 60 mM of cold $M_4N$. At the specified time post-injection, the mice were sacrificed, the organs and blood were collected, weighed, then dissolved overnight in 4 M guanidine isothiocyanate (GITC). The insoluble pellet was then further extracted with EtOH. Tritium content of both the GITC extract and the EtOH extract was measured on a Packard scintillation counter and the quantity of $M_4N$ in each organ was calculated based on the specific activity of the inoculum.

Tissue Distribution and Toxicity Analysis Following Short-Term and Long-Term Oral Feeding. For short-term feeding experiments, 30 mg of $M_4N$ dissolved in 300 µL castor oil was orally administered to each of 6 mice. At 2 h, 4 h, and 8 h post-administration time points, 2 mice were sacrificed, the organs and blood were collected, and the $M_4N$ extracted and quantitated as described below. In long-term feeding experiments, mice were fed food balls consisting of $M_4N$ dissolved in corn oil and Basal Mix (Harlan Teklad; Madison, Wis.; Cat. # TD 02273) for 14 weeks. Food balls weighed 9 g and contained 242 mg $M_4N$ each. Two mice, one male and one female, were reserved for long-term drug retention studies; and fourteen mice, both male and female, were used for long-term drug toxicity studies. At the end of feeding, mice were sacrificed, the organs and blood were collected, and the $M_4N$ extracted and quantitated as described below.

$M_4N$ Extraction and HPLC Analysis Following Oral Feeding. Organs and blood were harvested from $M_4N$-fed mice, then frozen overnight at −80° C. Prior to freezing, gastrointestinal organs (stomach, small intestine, colon) were cut open longitudinally and washed thoroughly with PBS to remove any contents. The following day, organs were cut into small pieces on dry ice with a razor blade, dried in a Speedvac, then crushed into a rough powder using a mortar and pestle. Samples were extracted overnight in 100% ethanol with shaking. Samples were centrifuged and the supernatant collected. Pellets were extracted two more times in 100% ethanol overnight with shaking. The pooled ethanol extracts were evaporated on bench top for several days, then re-extracted with ethyl acetate, and dried completely in a Speedvac. The dried samples were then analyzed quantitatively by HPLC and $M_4N$ was identified by mass spectroscopy using pure $M_4N$ as a standard.

In samples from short-term fed mice, dialysis was performed to further purify $M_4N$ from the tissue extracts. Dried ethanol extracts were redissolved in 1.5 mL 100% EtOH and centrifuged for 5 min. The supernatant was collected and the pellet was resuspended in 0.4 mL ethanol and centrifuged again. The supernatant was pooled with the previous supernatant, then dialyzed overnight against 150 mL 100% EtOH. The dialysates were dried on bench top and in a speed-vac, then analyzed by HPLC.

HPLC Quantitation of $M_4N$. Samples from a single mouse at each time point were sent to KP Pharmaceuticals (Bloomington, Ind.) for HPLC analysis. HPLC conditions were described as follows: 35%:0.1% TFA in $H_2O$, 65%="CAN." The $M_4N$ standard was prepared by diluting 10.01 mg $M_4N$ in 100 mL of CAN, then sonicating for 5 min. (2002 ng/injection). The samples were prepared by adding 400 µL EtOH and sonicating for 2 min. or until complete dissolution was achieved. The injection volume for the samples was 100 µL.

$M_4N$ is Distributed Systemically to Various Tissues and With No Detectable Toxicity Following Intraperitoneal, Intravenous, and Oral Administration Systemic Distribution of $M_4N$ Following a Single Intraperitoneal or Intravenous Administration Previous studies demonstrated substantial tumoricidal activity following localized intratumoral injection of $M_4N$ into C3 cell-induced tumors in mice, as described in U.S. Pat. No. 6,608,108. Yet, with few exceptions, the clinical use of nonsystemic intratumoral chemotherapy is rare even for high mortality cancers characterized by well defined primary lesions i.e. breast, colorectal, lung, and prostate. Rather, the conventional wisdom and standard of care in clinical oncology remains surgery followed by systemic chemotherapy and/or radiation as deemed appropriate to the clinical situation. Because the effective treatment of many primary tumors as well as metastatic disease requires systemic delivery, the ability to distribute $M_4N$ systemically in vivo was assessed.

A mixture of tritiated and cold $M_4N$ was dissolved in a 6% Cremaphor EL, 6% ethanol, 88% saline solvent then injected intraperitoneally (i.p.) and intravenously (i.v.) via tail vein into mice. At 3 hours post-injection, the organs and blood were harvested and weighed, and the $M_4N$ was extracted. The tritium content of the extracts from each organ was measured on a Packard scintillation counter and the quantity of $M_4N$ in each organ was calculated based on the specific activity of the inoculum. As shown in FIGS. 1A and 1B, $M_4N$ was successfully distributed to various organs at 3 hours post-injection by both i.p. and i.v. routes of administration. Interestingly, very similar profiles of tissue distribution were obtained despite the different routes of administration, thus indicating a nonrandom, perhaps regulated mechanism of drug dispersal. Corroborating this, a very similar profile of distribution was observed using an oral route of administration described below. The majority of the recovered radioactivity localized to the gastrointestinal tract organs (FIG. 1A): the stomach, small intestine, caecum, and large intestine, in the range of 3 µg to 20 µg of $M_4N$ per gram of tissue. Significant quantities of $M_4N$ were also present in the liver and fat, and lower concentrations in the range of 150 to 400 ng per gram tissue (FIG. 1B) were detected in the brain, kidneys and spleen. Little or no $M_4N$, however, was detected in the heart or the blood at 3 hours post-injection. In conclusion, $M_4N$ may be safely and systemically administered to various specific tissues via i.p. or i.v. injection.

Figure 2:
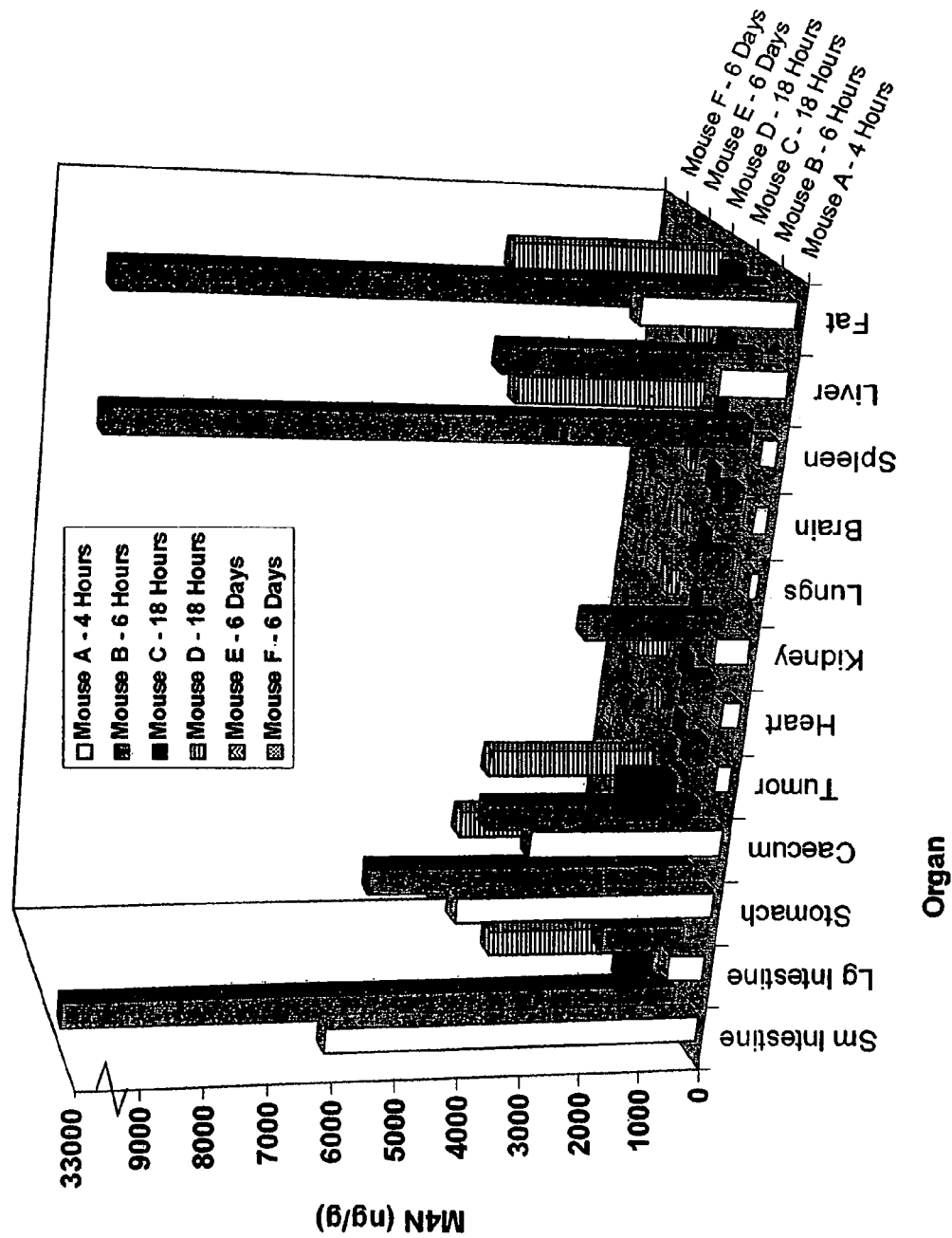
FIG. 2 shows systemic tissue distribution profile of $M_4N$ at various time points. Mice were injected with 100 μCi of $^3H$-$M_4N$ and 60 mM of unlabeled $M_4N$. Organs and blood were harvested and weighed at 4, 6, 18 hours and 6 days post-injection and the $M_4N$ was extracted. The tritium content of the organ extracts were measured, and the quantity of $M_4N$ in each organ was calculated based on the specific activity of the inoculum.

The previous experiment demonstrated that $M_4N$ may be delivered systemically and relatively rapidly to various tissues at a single time point. To determine the distribution of $M_4N$ in tissues over time following a single application, and also to assess the ability to deliver $M_4N$ to a distant tumor, six C3 cell-induced tumor bearing mice (A-F) were treated i.p. with $^3H$-$M_4N$ as described above. At 4 hours, 6 hours, 18 hours, and 6 days post-injection, the quantities of $^3H$-$M_4N$ in various tissues and the tumors were measured. The results shown in FIG. 2 confirmed the ability to distribute $M_4N$ systemically, with the majority of $M_4N$ again localizing to the GI tract organs, fat and liver, and lesser amounts detected in the brain and kidneys. Interestingly, and not apparent in the previous 3 hour injection, the fat and spleen exhibit a rapid increase in $M_4N$ levels between 4 hours and 6 hours. A significant, although relatively low amount of $M_4N$, 294 ng $M_4N$ per gram of wet tumor, was measured in the tumor at 6 hours post-injection. The changes in tissue distribution of $M_4N$ following initial application show an increase in $M_4N$ levels in these tissues from 0 to 6 hours with a peak occurring at approximately 6 hours. At 18 hours, $M_4N$ levels had substantially decreased, and at 6 days post-injection, although significant $M_4N$ levels could still be detected in most tissues, $M_4N$ levels had decreased to 5-10% of levels seen at 6 hours.

Systemic Tissue Distribution Following Short-Term and Long-Term Oral Feeding and In Vivo Toxicity Evaluations.

The previous experiments demonstrated that $M_4N$ can be systemically distributed in vivo by i.p. and i.v. injection with no apparent toxicity. The convenience and ease of oral administration, however, especially in the case of long-term postsurgical adjuvant treatment, would considerably facilitate drug administration to patients and would improve patient quality of life. Thus, in addition to i.p. and i.v. administration, the ability to systemically distribute $M_4N$ by oral administration was also investigated. In both short-term (<8 hours) feeding experiments and long-term (14 weeks) feeding experiments, $M_4N$ levels in various tissues and their in vivo toxicity was assessed. In short-term experiments, mice were fed 30 mg of $M_4N$ dissolved in castor oil (100 mg $M_4N$/mL castor oil), and at 2, 4, and 8 hours post-feeding, the quantity of $M_4N$ present in various tissues was determined by HPLC. As shown in Table 1, a relatively very low quantity of $M_4N$ (<2 ng per gram tissue) was found in each tissue at 2 hours post-feeding. Between 2 and 4 hours post-feeding, most organs including the liver, pancreas, kidneys, seminal vesicles, small intestine, stomach, large intestine, caecum, and blood exhibited a large increase in $M_4N$ levels. At 4 hours, as was seen in the i.p. and i.v. administrations, most of the $M_4N$ localized to the gastro-intestinal tract organs, in the range of 4 ng to 45 ng of $M_4N$ per gram of tissue. Significant quantities of $M_4N$ were also present in the pancreas, and lower concentrations in the range of 0.1 ng to 2 ng per gram tissue were detected in the heart, liver, seminal vesicles, blood, and bladder. At 8 hours post-feeding, $M_4N$ levels had decreased in nearly all organs, and most of the organs had been cleared of $M_4N$. In conclusion, $M_4N$ was distributed transiently to various organs following a single oral administration of 30 mg of $M_4N$. $M_4N$ levels peaked at roughly 4 hours post-feeding, and $M_4N$ concentrations were significantly lower than seen in i.p. and i.v. single administrations.

TABLE 1

| Organ | $M_4N$ (ng)/organ dry weight (g) | | | $M_4N$ (μg/g) |
|---|---|---|---|---|
| | 2 hours | 4 hours | 8 hours | 14 weeks |
| Heart | 0.83 | 0.11 | 1.16 | 12.62 |
| Liver | 0.05 | 0.52 | 0 | 5.89 |
| Lungs | 0.43 | 0 | 2.7 | 23.09 |
| Pancreas | 0.57 | 24.69 | 2.97 | 28.81 |
| Kidneys | 0.12 | 0.61 | 0 | 8.33 |
| Seminal Vesicles | 0.21 | 0.37 | 0 | 16.79 |
| Small Intestine | 0.09 | 8.42 | 5.53 | 906.27 |
| Stomach | 0.23 | 45.03 | 33.9 | 409.27 |
| Lg. Intestine | 0.24 | 8.24 | 2.68 | 350.88 |
| Caecum | 1.11 | 4.38 | 6.55 | 440.23 |
| Spleen | 1.1 | 0.16 | 0 | 302.78 |
| Blood | 0.5 | 2.08 | 0 | 23.13 |
| Bladder | 2.34 | 1.69 | 0 | 6.24 |
| Fat | 0.11 | 0 | 0 | 17.41 |

The objective of the long-term feeding experiments was to measure the steady state levels of $M_4N$ in various mouse organs following continuous oral administration for 14 weeks. Food balls weighing approximately 9 g and containing approximately 280 mg $M_4N$ were continually fed to wild-type mice for 14 weeks. A single 9 g food ball is consumed by a single mouse in about 3 days, which translates to 93.3 mg of $M_4N$ consumed or administered daily. HPLC quantitation showed that oral administration had systemically distributed $M_4N$ to all organs analyzed; and surprisingly had accumulated in all organs to concentrations greatly exceeding those seen previously for i.p., i.v., and oral one time administrations. Between 350 μg and 900 μg $M_4N$ per gram tissue was measured in the GI tract organs and the spleen; 15 μg/g to 30 μg/g $M_4N$ was measured in the lungs, pancreas, seminal vesicles, blood, and fat; and 5 μg/g to 13 μg/g $M_4N$ was measured in the heart, liver, kidneys, and bladder.

Figure 3:
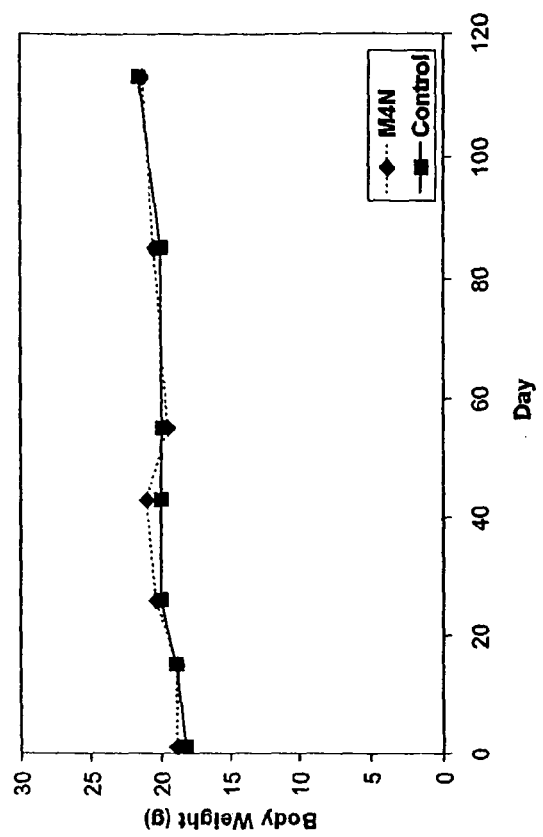
FIG. 3 shows the body weights of mice during long-term oral feeding of $M_4N$, indicating no apparent toxicity. Male and female mice were continually fed food balls weighing 9 g and containing 280 mg of $M_4N$ for 14 weeks. On average, mice consumed 93.3 mg of $M_4N$ per day. Control mice were fed food balls containing no $M_4N$. Body weights were recorded periodically.
Figure 3:
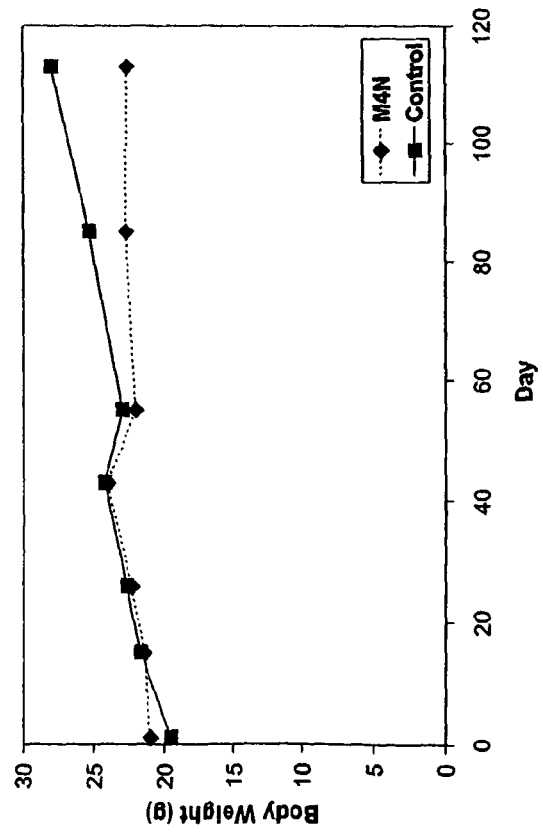

Despite the high levels of $M_4N$ present in various organs following systemic long-term oral administration, no signs of toxicity were seen as determined by daily evaluation of activity and overall body weight change (FIG. 3).

Systemic $M_4N$ treatment inhibits the in vivo growth of human tumor xenografts.

Based on (1) our cell culture analyses showing that $M_4N$ will effectively prevent the growth of various human tumor cells, and (2) our in vivo observations that $M_4N$ can be distributed systemically at non-toxic doses, we investigated whether systemic administration of $M_4N$ would inhibit the in vivo growth of human tumors. Athymic nude mice were implanted s.c. in each flank with MCF-7 breast adenocarcinoma cells, Hep3B hepatocellular carcinoma cells, HT-29 colorectal carcinoma cells, and LNCaP prostate carcinoma cells. Most mice developed tumors in both flanks, although some developed a single tumor. When tumors attained a mean diameter of 7-8 mm, mice received for three weeks a single daily i.p. injection containing 2 mg of $M_4N$ dissolved in 100 uL Cremaphor-ethanol based solvent. Control mice received vehicle only. Tumors were measured in two perpendicular dimensions (L and W) once every seven days, and tumor volumes were calculated according to the formula: $V=(L \times W/2)^3 \times \pi/6$.

Figure 4:
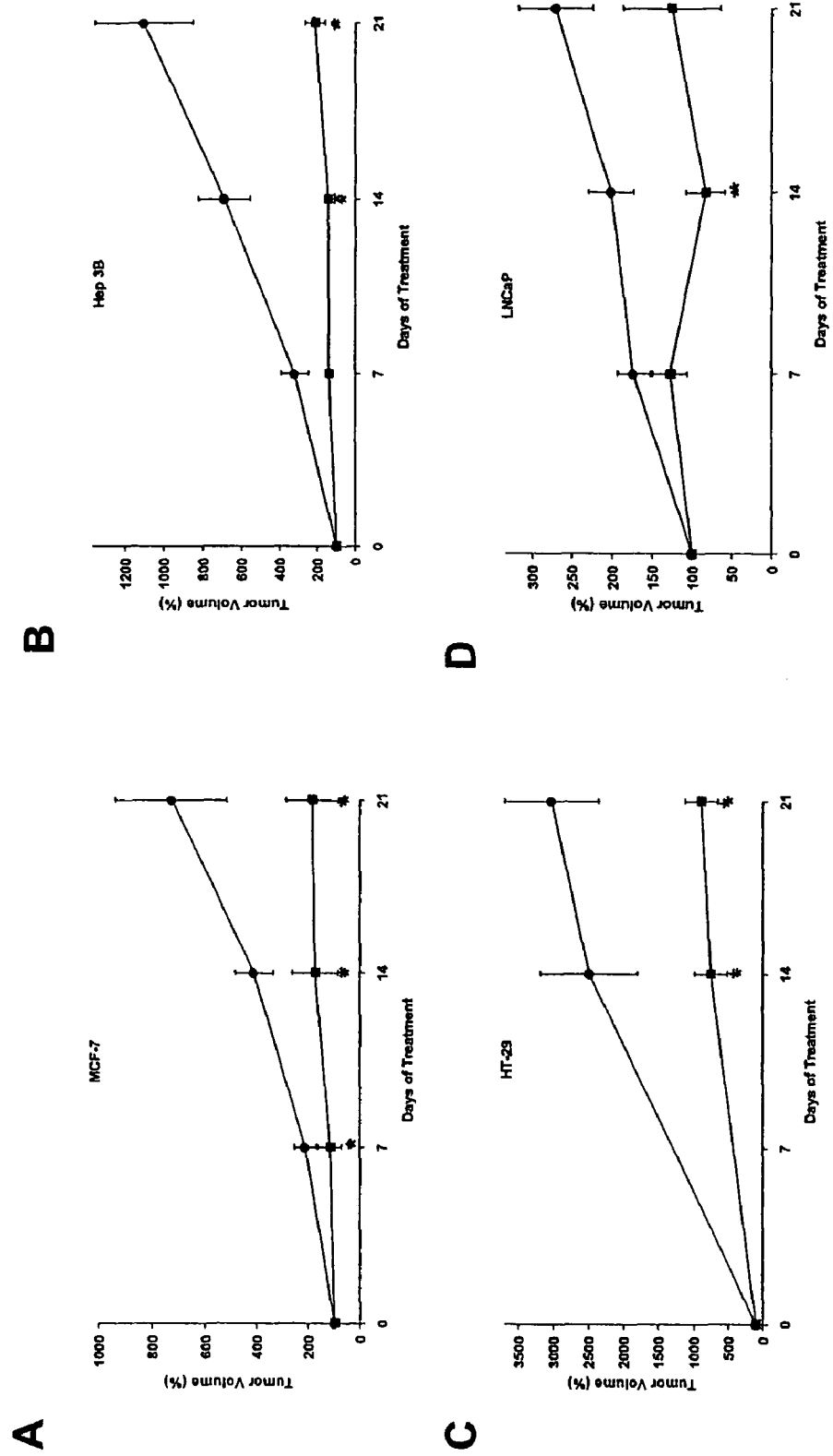
FIG. 4 shows that systemic treatment with $M_4N$ inhibits the in vivo growth of human tumor xenografts. Athymic nude mice were implanted s.c. in each flank with MCF-7 breast adenocarcinoma cells, Hep3B hepatocellular carcinoma cells, HT-29 colorectal carcinoma cells, and LNCaP prostate carcinoma cells. When tumors attained a mean diameter of 7-8 mm, mice received for three weeks a single daily i.p. injection containing 2 mg of $M_4N$ dissolved in 100 μL Cremaphor-ethanol based solvent. Control mice received vehicle only. Tumors were measured in two perpendicular dimensions (L and W) once every seven days, and tumor volumes were calculated according to the formula: $V=(L\times W/2)^3 \times \pi/6$.
Figure 5:
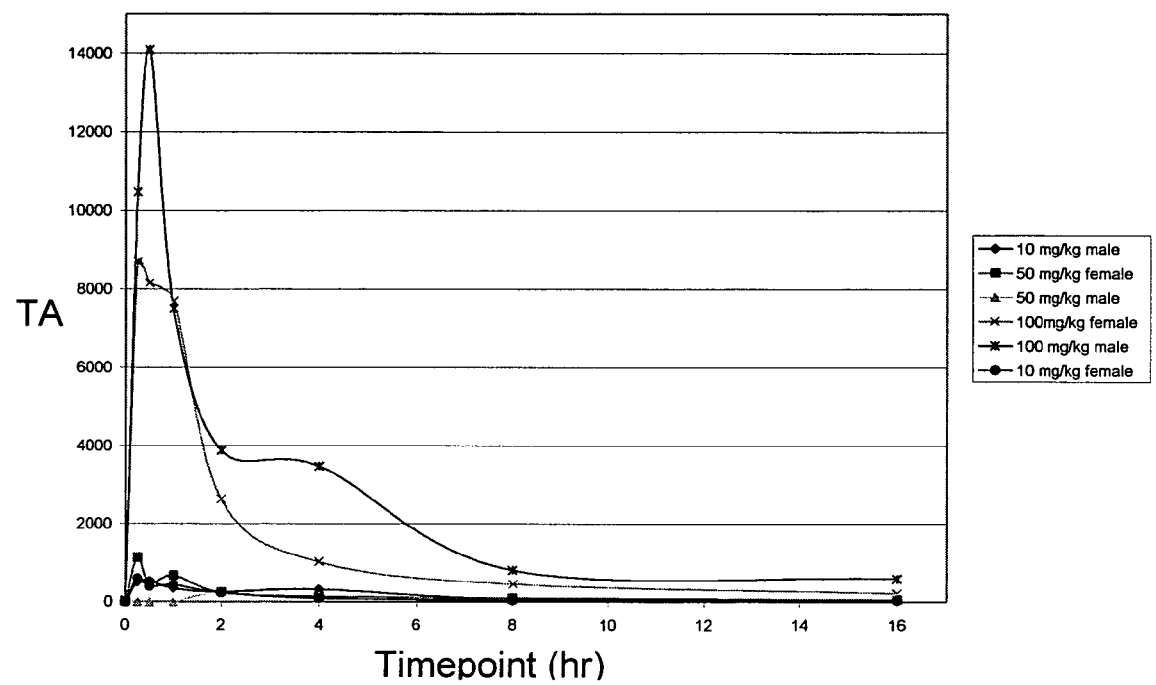
FIG. 5 shows the serum concentration of $M_4N$ in dogs given different doses of $M_4N$ at different time points.
Figure 6:
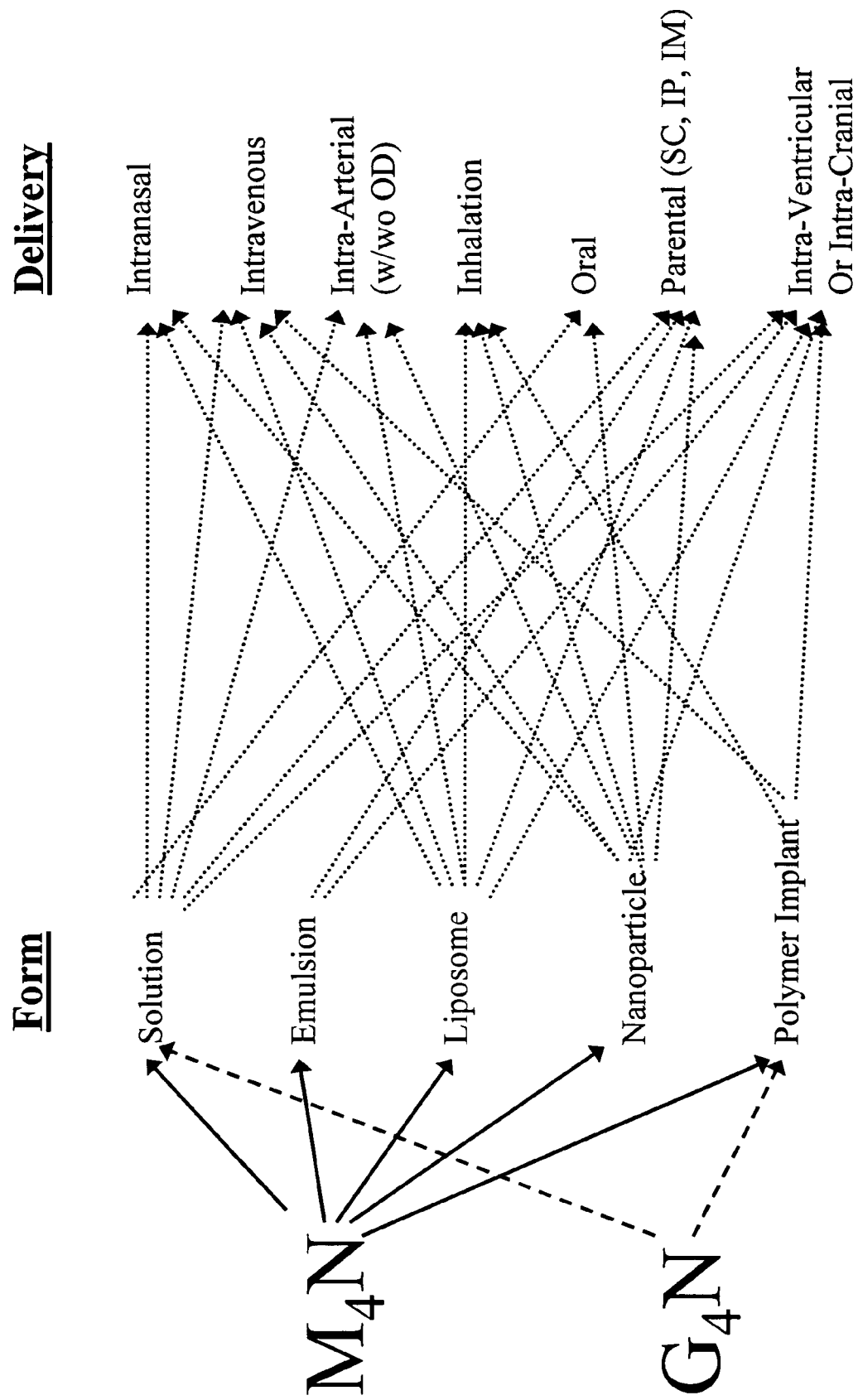
FIG. 6 is a schematic representation of examples of different modes of delivery of the NDGA derivatives to the brain for treatment of brain tumors. $M_4N$ represents a hydrophilic NDGA and $G_4N$ represents a lipophilic NDGA. OD represents osmotic disruption of blood brain barrier. SC represents subcutaneous administration. IP represents intraperitoneal administration. IM represents intramuscular administration.
Figure 7:
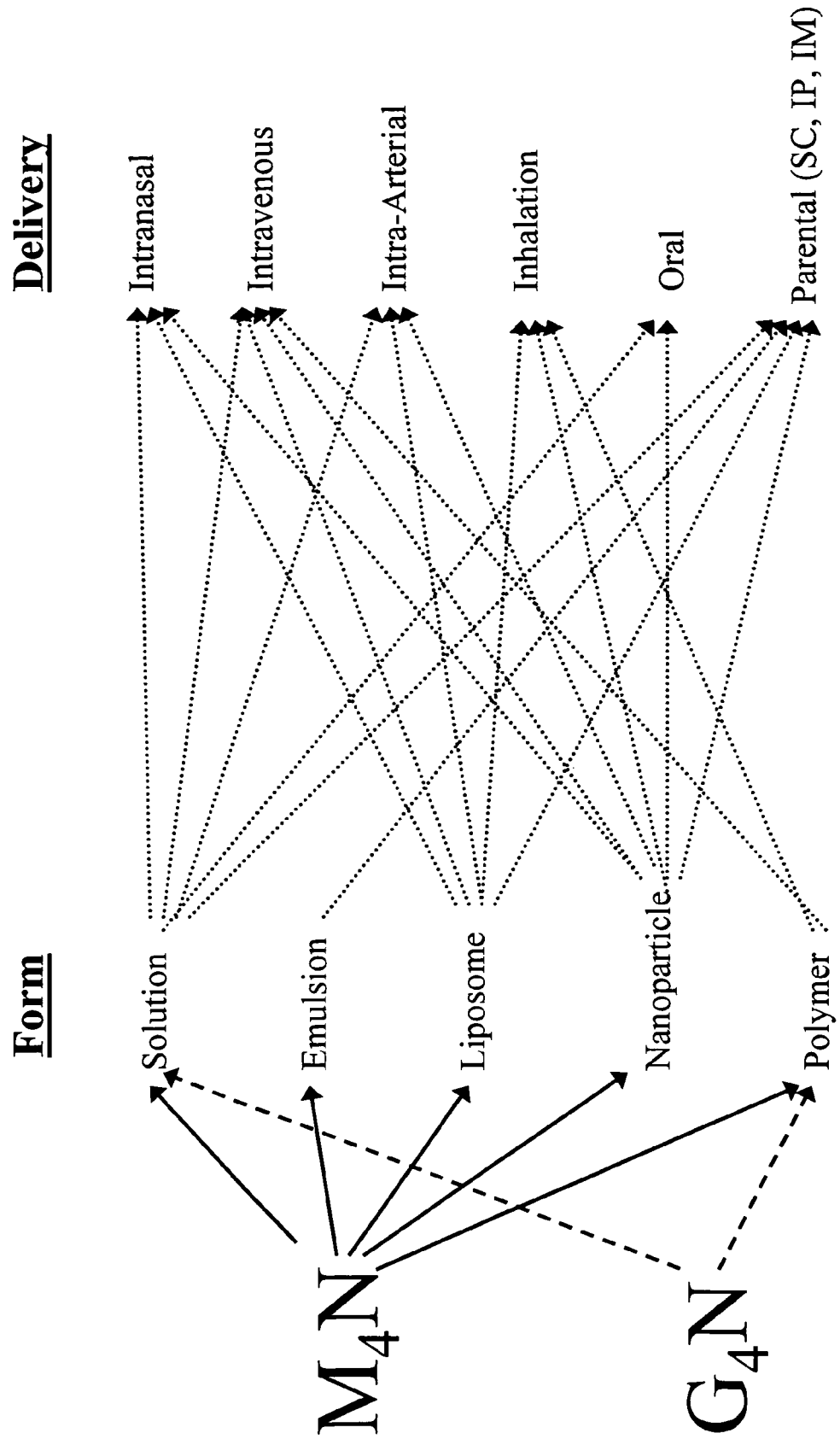
FIG. 7 is a schematic representation of examples of different modes of delivery of the NDGA derivatives to tissues other than the brain for the treatment of tumors. $M_4N$ represents a hydrophilic NDGA and $G_4N$ represents a lipophilic NDGA. SC represents subcutaneous administration. IP represents intraperitoneal administration. IM represents intramuscular administration.

As shown in FIG. 4, systemic $M_4N$ treatment for 21 days resulted in statistically significant (p<0.05) reductions in mean tumor growth in all four tumor types. After 21 days of systemic $M_4N$ treatment, MCF-7 tumors were reduced 74% in mean tumor volume to being only 25.5% of the mean volume of the control tumors (Table 2); HT-29 tumors were reduced 70% in mean volume; Hep 3B liver tumors were reduced 80%; and LNCaP prostate tumors were reduced 53%.

TABLE 2

| | Tumor Volume Increase (%) - 21 Days Treatment | | |
|---|---|---|---|
| Tumor Type | $M_4N$-Treatment | Control | Ratio of Mean $M_4N$-Treated Tumor Size to Control Tumor Size |
| McF-7 | 84% | 624% | 25.5% |
| Ht-29 | 787% | 2920% | 29.4% |
| Hep 3B | 113% | 1001% | 19.3% |
| LNCaP | 25% | 171% | 46.3% |

Table 3 shows the total number of tumors in each treatment group, and categorizes each based on whether there was an overall increase or decrease in size over the 21 days of treatment. In all four tumor types, 100% of the control tumors each exhibited an increase in tumor size. However, among the $M_4N$-treated mice, 7 out of 10 MCF-7 tumors decreased in size; 2 out of 7 Hep3B tumors decreased in size, 3 out of 11 HT-29 tumors decreased in size, and 9 out of 11 LNCaP tumors decreased in size following 21 days of systemic $M_4N$ treatment. In sum, 100% of the 47 control tumors increased in size, whereas 53%, or 21 out of 39, $M_4N$-treated tumors decreased in size following 21 days of systemic treatment; of the remaining 18 out of 39 $M_4N$-treated tumors, although increasing from their starting tumor size, most exhibited interrupted growth during the 21 days of treatment. Despite the significant tumoricidal effect observed for each tumor type, body weights and the general health of the mice were monitored over the 21 day course of treatment and indicated no toxicity in any of the mice.

TABLE 3

| Treatment | Tumor Type | Total # Tumors | IOTV | DOTV |
|---|---|---|---|---|
| Control | MCF-7 | 7 | 7 | 0 |
| | Hep 3B | 6 | 6 | 0 |
| | HT-29 | 24 | 24 | 0 |
| | LNCaP | 10 | 10 | 0 |
| | | 47 (100%) | 47 (100%) | 0 (0%) |
| $M_4N$ | MCF-7 | 10 | 3 | 7 |
| | Hep 3B | 7 | 5 | 2 |
| | HT-29 | 11 | 8 | 3 |
| | LNCaP | 11 | 2 | 9 |
| | | 39 (100%) | 18 (46%) | 21 (53%) |

IOTV: Increase in Volume from the Original Tumor Volume
DOTV: Decrease in Volume from the Original Tumor Volume Example 14

Safety Studies in Humans

In this example, the inventors demonstrated clear safety and efficacy of NDGA derivative delivery in humans as a therapy for head and neck cancer. This example describes the results of two separate clinical studies that spanned range of patient ages, stages of disease development, and two different treatment methods. This example demonstrates the following: (1) $M_4N$ can be delivered by escalating doses up to about 495 mg weekly for three weeks or at dosages of 20 mg per day for up to five days without drug-related toxicity. This daily delivery of $M_4N$ can be with or without concomitant therapy with $G_4N$ at a dose of 20 mg per day for up to five days and is followed by surgical resection of the lesion; (2) Both of these treatment methods delivered over 80% efficacy in terms of induction of necrosis in patients that completed the treatments; (3) In long-term follow ups of the ex-US study 64% of patients remained disease free and also free from long term effects of NDGA-derivative exposure.

US Phase I Intratumoral Head and Neck Cancer Study:

A Phase I clinical study has been completed under a US IND. Mean subject age was 66 years (range 53 to 82 years). Eight male subjects and one female subject participated. Mean weight was 139 lbs. (range 102 to 219 lbs.). All patients were diagnosed with refractory head and neck carcinomas.

Nine (9) subjects were dosed with an intratumoral dose of $M_4N$ given weekly for three weeks, at doses of 5 mg/cm$^3$ tumor volume (2 subjects), 10 mg/cm$^3$ (2 subjects) 15 mg/cm$^3$ (3 subjects) and 20 mg/cm$^3$ (2 subjects). Doses up to 495 mg weekly for three weeks were administered.

Three subjects completed the study per protocol. Two subjects died on study from causes considered unlikely to be related to study medication. One subject withdrew consent after receiving three doses of $M_4N$ as he could not travel to meet protocol requirements. One withdrew consent after experienced severe radiating pain on injection associated with an accidental perineural dose. One was withdrawn after a single dose as his tumor was considered to be too close to the carotid artery to allow a safe second dose. One was withdrawn as a result of tumor progression. Dosing related adverse events were otherwise minor and included mild or moderate pain on injection (4 subjects). No other adverse events were attributed to $M_4N$ administration. Sporadic, and non-reproducible mild elevations in LFTs were seen in 2 subjects, which resolved while still on therapy. No changes attributable to drug were seen in hematology parameters.

Six (6) Serious Adverse Events (SAE) were reported in four (4) subjects. Serious adverse events included supraventricular tachycardia (two episodes on separate occasions in one subject), pneumonia, dehydration and death from tumor progression (one subject), and death 19 days after study (cause unknown). In all cases, the SAE's were considered unlikely or not related to study medication.

In 5 of 6 subjects receiving three doses, drug related tumor necrosis occurred after injection. No damage occurred to healthy tissue surrounding the tumor. Fistula formation developed where tumors were full thickness. Tumors also were noted to have softened, or "pancaked", but residual tumor at the margins continued to grow, suggesting that systemic administration may be more appropriate. Tumor volume reduction was radiologically confirmed in three of the six patients completing three doses. Dosing was generally well tolerated.

Example 15

Safety Studies in Beagle Dogs Following 14-Day Intravenous Infusion of $M_4N$

In this example the Maximal Tolerable Dose (MTD) of two different formulations of $M_4N$ [Cremaphor-Ethanol (CET) or Dimethyl Sulfoxide (DMSO)] to male and female beagle dogs was determined. This example shows that $M_4N$ was safely administered by intravenous infusion into dogs over four hours at doses up to 10 mg/kg with a CET vehicle or up to 100 mg/kg with a DMSO vehicle. Blood levels of up to 14,000 ng/ml $M_4N$ were achieved with these formulations with minimal toxicity.

Vascular Access Port (VAP) Implantation Surgery for $M_4N$-CET Group

VAPs were implanted into beagle dogs such that the tip of the infusion catheter was situated at the level of the superior vena cava. Dogs were treated prophylactically with an analgesic and antibiotic on the day of surgery and with antibiotics and/or analgesics following surgery (according to Gene Logic Inc. SOP Nos. 324.0.2, 325.0.1, and 326.0.2, as appropriate.) Other treatments were provided as recommended by the staff veterinarian. The catheter lines were flushed with saline during the postoperative recovery period with a frequency deemed appropriate by the Study Director.

Although VAPs were implanted into dogs that were assigned to receive infusion of $M_4N$-DMSO, however, DMSO was found to be not compatible with the infusion catheter attached to the VAP inside the animals. Thus the $M_4N$-DMSO group animals were administered with $M_4N$-DMSO with eight intravenous injections via the non-VAP jugular vein every 30 minutes over a 4-hour period. This frequency of delivery mimicked the delivery of the test article using the infusion pump.

TABLE 4

Group Designation and Dose Levels

| Treatment | Number of Dogs | Dose Level (mg/kg) | Infusion Rate (mL/kg/hr) | Injection Volume (mL) | Duration |
|---|---|---|---|---|---|
| $M_4N$-CET | 1M, 1F | 0 | M (1.7), F (1.3) | | 2 hours |
| | | 1 | M (1.7), F (1.4) | | 2 hours |
| | | 5 | M (0.7), F (0.6) | | 4 hours |
| | | 10 | M (1.8), F (1.3) | | 4 hours |
| $M_4N$-DMSO[a] | 1M, 1F | 0 | | M(0.17), F(0.12) | 4 hours |
| | | 10 | | M(0.16), F(0.13) | 4 hours |
| | | 50 | | M(0.83), F(0.66) | 4 hours |
| | | 100 | | M(1.78), F(1.35) | 4 hours |
| $M_4N$-DMSO[b] | 1M, 1F | 200 | | M(4.1), F(2.8) | ~1 hour |

[a] 8 intravenous injections every 30 minutes over 4 hours
[b] Additional animals to determine potential toxicity, M received 3 injections, F received 2 injections Animals from the CET group were observed during the entire infusion period and for at least one hour following end of infusion. The dogs in the DMSO group were observed throughout the jugular vein injection period and for at least one hour following the last (eighth) injection.

Blood Sample Collection for Toxicokinetic (TK) Analysis

Blood samples from the CET group animals were collected via the jugular vein on Study Day (SD) 1, SD 3, SD 6, and SD 8 at the following timepoints: predose, 0.25, 0.5, 1, 2, 4, 8, and 16 hours following the completion of the approximate 4-hour infusion.

Blood samples from the DMSO group animals were collected via the cephalic vein on SD 1, SD 3, SD 6, and SD 8 at the following timepoints: predose, 0.25, 0.5, 1, 2, 4, 8, and 16 hours following the final injection dose of $M_4N$-DMSO.

Blood samples collected from both groups of animals were processed for plasma and serum for TK analysis.

TK Analysis

The plasma and serum samples were sent to MedTox Laboratories, the Sponsor's designated laboratory for TK analysis.

TK analysis of $M_4N$ plasma and serum concentration-time data was performed using a validated method (M200406) by MedTox Laboratories and analyzed by noncompartmental methods to obtain estimates of toxicokinetic parameters (where data allow), but not necessarily limited to, Cmax, Tmax and AUC.

Study Day 1 (SD1):

a) $M_4N$-CET Group

Male dog: reacted to CET infusion with erythema, hives, itchiness, emesis, diarrhea, and general lethargy in the first hour and a half. He began to recover after that, started walking around, drinking water. He behaved normally soon following end of infusion. Female dog: reacted similarly to the male dog except without emesis and diarrhea. Her allergic reactions were also less severe than the male. She behaved normally soon following end of infusion.

b) $M_4N$-DMSO Group

Male dog: reacted to DMSO with slight erythema, slight itchiness, otherwise normal. Behavior was normal soon following end of last injection. Female dog: reacted similarly to the male dog. Her behavior was normal soon following end of last injection.

All 4 dogs survived the infusion of their respective vehicle treatment. They all appeared fine and behaved normally following treatment.

Study Day 3 (SD3):

a) $M_4N$-CET Group

Male dog: reacted to $M_4N$-CET (1 mg/kg) infusion with slight erythema, hives, itchiness. The reactions this day were milder than those on SD1. In particular, the animal did not have emesis, diarrhea, or lethargy, he was more alert than on SD1. He behaved normally soon following end of infusion. Female dog: her reactions to the $M_4N$-CET (1 mg/kg) infusion today was even milder than those observed on SD1. Her allergic reactions included mild erythema and itchiness, but she was generally quite alert throughout the 4-hr infusion period. She behaved normally soon following end of infusion.

b) $M_4N$-DMSO Group

Male dog: There was no adverse clinical reaction exhibited by this dog. There was, as expected, some irritation at the injection sites along the jugular vein.

Female dog: There was no adverse clinical reaction exhibited by this dog. There was, as expected, some irritation at the injection sites along the jugular vein.

All 4 dogs survived following administration of their respective test article treatment. They all appeared fine and behaved normally following treatment.

Study Day 6 (SD6):

a) $M_4N$-CET Group

Male dog: Similar to the previous two dosing days, this animal reacted to the infusion with slight erythema, hives, and itchiness. The intensity of the reactions was certainly no more than the reactions on SD3. He did not vomit or had diarrhea, was generally alert throughout the infusion period. He behaved normally soon following end of infusion.

Female dog: Consistent with her reactions to previous dosings, she tolerated today's infusion better than the male dog, she still had mild erythema and itchiness, but she was quite alert. She behaved normally soon following end of infusion.

b) $M_4N$-DMSO Group

Male dog: This dog was successfully injected intravenously with $M_4N$-DMSO via the non-VAP jugular vein for the first 3 dosing intervals (1/2 hr between doses). As with the previous dosing days, this dog did not show any adverse clinical signs or symptoms following each injection. Prior to the fourth injection, the technicians noticed a swelling "the size of an egg" around the injection site. Subcutaneous misdose could be ruled out because it would have been easily detected during the 3rd injection. It was most likely a hematoma as a result of slow extravasation of blood through the injection site. This animal did not receive any more dosing following the third injection, however, blood samples were collected, the exact time points of the blood collection post-third injection dose was clearly documented. The hematoma resolved within two hours and gentle massaging of the injection site area did not irritate the animal.

Female dog: This dog was successfully injected with $M_4N$-DMSO for the entire 8 repeated injections over 4 hours. Similar to the previous dosing days, this dog did not show any adverse clinical signs or symptoms Study Day 8 (SD8):

a) $M_4N$-CET Group

Both male and female dogs received full dose. Their reactions to this high dose were similar to those exhibited in previous dosing days, which include erythema, hives, and itchiness. No vomiting or diarrhea was noted. The animals behaved normally soon following end of infusion.

b) $M_4N$-DMSO Group

Both the male and female dogs received full dose. Their reactions to the high dose were similar to those on previous dosing days. There appeared to be more G.I. irritation as both dogs showed some retching reaction without vomiting, they were more lethargic than usual. However, both dogs survived the full high-dose administration regimen and appeared to have recovered following the end of dosing.

Additional Dose (200 mg/kg) for $M_4N$-DMSO Group

Since animals dosed with $M_4N$-DMSO at 100 mg/Kg did not show adverse clinical signs or symptoms, two spare dogs (1 male, 1 female) were dosed with $M_4N$-DMSO at 200 mg/Kg. At 200 mg/Kg, the female dog experienced difficulty breathing (with nasal frothing) after only the first of eight doses, she soon collapsed but was able to recover for the second dose. After the second dose, her reaction was similar but even more severe. Thus the staff veterinarian suggested euthanizing the female dog. The male dog was slightly more tolerant but exhibited similar difficulty breathing signs and collapsing symptoms. He received a total of three doses and the staff veterinarian suggested further dosing be stopped.

There were no post-dose TK analysis for this additional dosing, all pre-dose blood samples collected today were discarded.

TK Analysis a) $M_4N$-CET Group

TABLE 5

$M_4N$-CET - SERUM RESULTS (NG/ML)

| Animal No./Sex | Dose | Predose | 15 min | 30 min | 1 hr | 2 hr | 4 hr | 8 hr | 16 hr |
|---|---|---|---|---|---|---|---|---|---|
| 10828F | 1 mg/kg | <2 | >100 | >100 | 78.59 | 48.32 | 39.75 | 9.88 | 4.33 |
| 10827M | 1 mg/kg | <2 | >100 | >100 | 53.78 | 32.72 | 26.65 | 7.19 | 4.63 |

TABLE 5-continued

M₄N-CET - SERUM RESULTS (NG/ML)

| Animal No./Sex | Dose | Predose | 15 min | 30 min | 1 hr | 2 hr | 4 hr | 8 hr | 16 hr |
|---|---|---|---|---|---|---|---|---|---|
| 10828F | 5 mg/kg | <1 | >100 | >50 | >50 | >50 | 34.40 | 19.45 | 11.57 |
| 10827M | 5 mg/kg | <1 | >50.0 | >50 | >50 | 45.35 | 19.99 | 12.98 | 6.71 |
| 10828F | 10 mg/kg | <20.0 | >1000 | >1000 | 705.47 | 285.10 | 187.82 | 133.50 | 52.94 |
| 10827M | 10 mg/kg | 63.76 | >1000 | >1000 | 783.86 | 431.21 | 158.20 | 117.00 | 60.36 |

In general, intravenous infusion of M₄N-CET at different dose levels for 4 hours resulted in extremely high serum concentrations at the early time points and peaked at 30 minutes following end of infusion (Table 5). The serum concentrations of the test article reduced over the next 15 hours.

b) M₄N-DMSO Group

TABLE 6

M₄N-DMSO - SERUM RESULTS (NG/ML)

| Animal No./Sex | Dose | Predose | 15 min | 30 min | 1 hr | 2 hr | 4 hr | 8 hr | 16 hr |
|---|---|---|---|---|---|---|---|---|---|
| 10831F | 10 mg/kg | <2 | 594.98 | 398.95 | 436.92 | 238.20 | 97.92 | 43.80 | 38.39 |
| 10832M | 10 mg/kg | <2 | 516.8 | 533.07 | 348.7 | 252.86 | 317.13 | 78.87 | 56.27 |
| 10831F | 50 mg/kg | 3.49 | 1136.51 | 474.95 | 673.4 | 241 | 144 | 101 | 58.8 |
| 10832M | 50 mg/kg | 19.91 | NR | NR | NR | 234.15 | 79.11 | 65.79 | 45.8 |
| 10831F | 100 mg/kg | 21.47 | 8688.10 | 8163.68 | 7696.48 | 2624.2 | 1021.05 | 459.82 | 222.22 |
| 10832M | 100 mg/kg | 38.22 | 10477 | 14088 | 7498.88 | 3878.86 | 3468.19 | 814.24 | 593.83 |

In general, repeated intravenous injection of M₄N-DMSO at different dose levels for 4 hours resulted in extremely high serum concentrations. The serum concentration data reported in Table 6 are the results following systematic dilution of the serum to accommodate detection range. The results showed that in general, the serum concentration of M₄N-DMSO was high in the early time points and peaked at 30 minutes following the last injection. The serum concentrations of the test article reduced over the next 15 hours. Based on the serum concentrations from this group, the half-life of M₄N-DMSO, when administered by repeated intravenous injection, was approximately 1.5 to 2 hours. It is noteworthy that from the pre-dose serum concentrations of M₄N-DMSO over the course of this MTD phase, there was a slight build-up of the test article in the blood, but this retention was generally less than 0.3% of the highest serum concentration.

The purpose of the MTD phase of this study was to determine the maximum tolerable dose of two different formulations of M₄N (Cremaphor-Ethanol or DMSO) to male and female beagle dogs. The group of animals that received M₄N-CET reacted with itchiness, erythema, hives, and sleepiness; clinical signs and symptoms consistent with the effects of Cremaphor-Ethanol. Animals that received repeated injections of M₄N-DMSO showed some irritation at the injection site and minor retching at 100 mg/kg. However, both animals collapsed following 2 or 3 injections of M₄N-DMSO at 200 mg/kg. TK analysis from this group suggested a half life for M₄N-DMSO in the range of 1.5-2 hours. There was minor build up of the test article over the course of the MTD phase, however, this retention only amounted to less than 0.3% of the maximum serum concentration. In conclusion, the MTD phase of this study was a success as the dose level that resulted in significant adverse clinical signs and symptoms was identified, thus the objective of this phase was achieved.

REFERENCES

Ansel, H. C. et al. (1999). Pharmaceutical Dosage Forms and Drug Delivery Systems eds., 7th ed., Lippincott, Williams, & Wilkins.

Armstrong, W. B. et al. (2000). Clinical modulation of oral leukoplakia and protease activity by Bowman-Birk inhibitor concentrate in a Phase IIa chemoprevention trial. Clin. Cancer Res. 6: 4684-4691.

Avgoustakis, K. et al. (2002). PLGA-mPEG nanoparticles of cisplatin: in vitro nanoparticle degradation, in vitro drug release and in vivo drug residence in blood properties. J. Controlled Release, 79: 123-135.

Beletsi, A. et al. (1999). Effect of preparative variables on the properties of PlGA-mPEG copolymers related to their application in controlled drug delivery, Int. J. Pharm. 182: 187-197.

Brem, H., and Gabikian, P. (2001). Biodegradable polymer implants to treat brain tumors. J. Control. Rel. 74: 63-67.

Choi, W. S. et al. (2001). Inhalation delivery of proteins from ethanol suspensions. Proc. Natl. Acad. Sci. USA, 98(20): 11103-11107.

Churchill, J. R., and Hutchinson, F. G. (1988). Biodegradable amphipathic copolymers. U.S. Pat. No. 4,745,160.

Cloughesy, T. F. et al. (1997). J. Neurononcol. 35: 121-131.

Desai, D. C. et al. (2001) Serum pancreastatin levels predict response to hepatic artery chemoembolization and somatostatin analogue therapy in metastatic neuroendocrine tumors. Reg Peptides 96: 113-117.

Doolittle, N. D. et al. (2000). Cancer 88(3): 637-647.

Drougas, J. G. et al. (1998) Hepatic artery chemoembolization for management of patients with advanced metastatic carcinoid tumors. Am. J. Surg. 175: 408-412.

Epstein, J. B., et al. (2001). Oral topical doxepin rinse: analgesic effect in patients with oral mucosal pain due to cancer or cancer therapy. Oral Oncol. 37: 632-637.

Epstein, J. B. et al. (2002). Fluconazole mouthrinses for oral candidiasis in post-irradiation, transplant, and other patients. Oral Surg. Oral Med. Oral Pathol. Oral Radiol. Endod. 93(6): 671-675.

Fessi, H., et al. (1989). Nanocapsule formulation by interfacial deposition following solvent displacement. Int. J. Pharm., 55: R1-R4.

Fleming, A. B. and Saltzman, W. M. (2002). Pharmacokinetics of the Carmustine Implant. Clin. Pharmacokinet., 41(6): 403-419.

Fu, J. et al. (2002). New Polymeric Carriers for Controlled Drug Delivery Following Inhalation or Injection. Biomaterials, 23: 4425-4433.

Gennaro, A. (1995). "Remington: The Science and Practice of Pharmacy", 19th edition, Lippincott, Williams, & Wilkins.

Gonda, I., et al. (1998). Inhalation delivery systems with compliance and disease management capabilities. J. Control. Rel. 53: 269-274.

Heller, J. D. et al. (2001). Tetra-O-methyl nordihydroguaiaretic acid induces G2 arrest in mammalian cells and exhibits turmoricidal activity in vivo. Cancer Res. 61: 5499-5504.

Hwu, J. R. et al. (1998). Antiviral activities of methylated nordihydroguaiaretic acids. 1. Synthesis, structure identification, and inhibition of Tat-regulated HIV transactivation. J. Med. Chem. 41(16): 2994-3000.

Kao, H. D., et al. (2000). Enhancement of the Systemic and CNS Specific Delivery of L-Dopa by the Nasal Administration of Its Water Soluble Prodrugs, Pharmaceut. Res., 17(8): 978-984.

Khouri, A. I., et al. (1986), Development of a new process for the manufacture of polyisobutyl-cyanoacrylate nanoparticles, Int. J. Pharm., 28: 125.

Kibbe, A. H. (2000). Handbook of Pharmaceutical Excipients, eds., 3$^{rd}$ ed. Amer. Pharmaceutical Assoc.

Kim, E. H. et al. (2004). Roscovitine sensitizes gliomas cells to TRAIL-mediated apoptosis by downregulation of survivin and XIAP. Oncogene 23: 446-456.

Kohori, F., et al. (1998). Preparation and characterization of thermally responsive block copolymer micelles comprising poly(N-isopropylacrylamide-b-D,L-lactide). J. Control. Rel. 55: 87-98.

Kohori, F., et al. (1999). Control of adriamycin cytotoxic activity using thermally responsive polymeric micelles composed of poly(N-isopropylacrylamide-co-N,N-dimethylacrylamide)-b-poly(D,L-lacide). Colloids Surfaces B: Biointerfaces 16: 195-205.

Kreuter, J. (1994), Nanoparticles, In Encyclopedia of Pharmaceutical Technology; Swarbick, J.; Boylan, J. C. Eds.; Marcel Dekker (New York, 1994), pp. 165-190.

Lamprecht, A., et al. (2001a), Biodegradable Nanoparticles for Targeted Drug Delivery in Treatment of Inflammatory Bowel Disease. J. Pharmacol. Experimental Therapeutics, 299: 775-781.

Lamprecht, A., et al. (2001b), Design of rolipram loaded nanoparticles: comparison of two preparation methods. J. Control. Rel., 71: 297-306.

Liggins, R. T. and Burt, H. M. (2002). Polyether-polyester diblock copolymers for the preparation of paclitaxel loaded polymeric micelle formulations. Adv. Drug Del. Rev. 54: 191-202.

Lockman, P. R., et al. (2002), Nanoparticle Technology for Drug Delivery Across the Blood-Brain Barrier. Drug Development Indus. Pharmacy, 28(1): 1-13.

Loganzo, F. et al. (2003). HTI-286, a synthetic analogue of the tripeptide hemiasterlin, is a potent antimicrotubule agent that circumvents p-glycoprotein-mediated resistance in vitro and in vivo. Cancer Res. 63: 1838-1845.

Madden, T. D., et al. (1990). Chem. Phys. Lipids 53: 37-46.

Mantriprgada, S. (2002). A lipid based depot (DepoFoam®) technology) for sustained relesase drug delivery. Prog Lipid Res. 41: 392-406.

Marttin, E. et al. (1997). Nasal absorption of dihydroergotamine from liquid and powder formulations in rabbits. J. Pharm. Sci. 86(7): 802-807.

McDonald, R. W. et al. (2001). Synthesis and anticancer activity of nordihydroguaiaretic acid (NDGA) and analogues. Anti-Cancer Drug Des. 16: 261-270.

Minn, A. et al. (2002). Drug transport into the mammalian brain: the nasal pathway and its specific metabolic barrier. J. Drug Target, 10: 285-296.

Mu, L. and Feng, S. S. (2003). A novel controlled release formulation for the anticancer drug paclitaxel (Taxol®): PLGA nanoparticles containing vitamin E TPGS. J. Control. Rel. 86: 33-48.

Pitten, F. et al. (2003) Do cancer patients with chemotherapy-induced leucopenia benefit from an antiseptic chlorhexidine-based oral rinse? A double-blind, block-randomized, controlled study. J. Hosp. Infect. 53(4): 283-291.

Rapoport, N. Y., et al. (1999). Micellar delivery of doxorubicin and its paramagnetic analog, ruboxyl, to HL-60 cells: effect of micelle structure and ultrasound on the intracellular drug uptake.

Sharma, U. S. et al. (1997). Liposome-mediated therapy of intracranial brain tumors in a rat model. Pharm. Res. 14(8): 992-998.

Song, C. X. et al. (1997). Formulation and characterization of biodegradable nanoparticles for intravascular local drug delivery, J. Controlled Release 43: 197-212.

Stuchlik, M. and Zak, S. (2001). Lipid-Based Vehicle for Oral Delivery, Biomed. Papers 145(2): 17-26.

Tuzar, Z. and Kratochvil, P. (1976). Block and graft copolymer micelles in solution. Adv. Colloid Interface Sci. 6:201-232.

Uckun, F. M. et al. (1999) Treatment of therapy-refractory B-lineage acute lymphoblastic leukemia with an apoptosis-inducing CD19-directed tyrosine kinase inhibitor. Clin. Cancer Res. 5: 3906-3913.

Wang, D. L. et al. (2000). Topical Delivery of 13-cis-Retinoic Acid by Inhalation Up-Regulates Expression of Rodent Lung but not Liver Retinoic Acid Receptors. Clin. Cancer Res. 6: 3636-3645.

Wilhelm, M. et al. (1991). Poly(styrene-ethylene oxide) block copolymer micelle formation in water: a fluorescence probe study. Macromolecules 24: 1033-1040.

Zhang, X. et al. (1996). Development of amphiphilic diblock copolymers as micellar carriers of taxol. Int. J. Pharm. 132: 195-206.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating a malignant, premalignant or benign tumor in a subject arising from or associated with a tissue or organ selected from the group consisting of breast, liver, stomach, pancreas, colorectal, colon and prostate, comprising the steps of:

(a) providing a composition comprising tetra-O-methyl NDGA and a pharmaceutically acceptable carrier or excipient; and (b) administering the composition to the subject;

wherein the composition is administered systemically by a route of administration other than by direct injection into or topical application onto the tumor, wherein the route of administration is selected from the group consisting of oral administration; inhalation administration; intra-arterial administration, with or without occlusion; intracranial administration; intraventricular administration; intravenous administration; intramuscular administration; implantation administration; and central venous administration.

2. The method of claim 1, wherein the composition is administered orally.

3. The method of claim 1, wherein the pharmaceutically acceptable carrier or excipient is an oil.

4. The method of claim 3, wherein the oil is castor oil or corn oil.

5. The method of claim 2, wherein the composition is present in an edible mix.

6. The method of claim 1, wherein the composition is administered daily.

7. The method of claim 6, wherein the composition is administered daily for 5 or more days to a week.

8. The method of claim 6, wherein the composition is administered daily for 5 or more days to 2 weeks.

9. The method of claim 6, wherein the composition is administered daily for 5 or more days to 3 weeks.

10. The method of claim 2, wherein the amount of tetra-O-methyl NDGA administered is at least 30 mg per dose.

11. The method of claim 2, wherein the amount of tetra-O-methyl NDGA administered is at least 90 mg per dose.

12. The method of claim 2, wherein the tetra-O-methyl NDGA is present in the composition at a concentration of 20 mg/mL.

13. The method of claim 1, wherein the pharmaceutically acceptable carrier or excipient comprises Cremaphor EL, ethanol and saline.

14. The method of claim 13, wherein the Cremaphor EL concentration is 6%.

15. The method of claim 13, wherein the ethanol concentration is 6%.

16. The method of claim 13, wherein the saline concentration is 88%.

17. The method of claim 13, wherein the composition administered to the subject comprises at least 2 mg of tetra-O-methyl NDGA per dose.

18. The method of claim 13, wherein the composition is administered intravenously.

19. The method of claim 1, wherein the composition is administered more frequently than once every 6 days.

20. The method of claim 19, wherein the composition is administered more frequently than once every 2 days.

21. The composition of claim 1 wherein the tumor is in the breast.

22. The composition of claim 1 wherein the tumor is in the liver.

23. The composition of claim 1 wherein the tumor is in the stomach.

24. The composition of claim 1 wherein the tumor is colorectal.

25. The composition of claim 1 wherein the tumor is in the colon.

26. The composition of claim 1 wherein the tumor is in the prostate.

27. The composition of claim 1 wherein the composition is administered via inhalation.

28. The composition of claim 1 wherein the composition is administered via intra-arterial administration, with or without occlusion.

29. The composition of claim 1 wherein the composition is administered via intracranial administration.

30. The composition of claim 1 wherein the composition is administered via intraventricular administration.

31. The composition of claim 1 wherein the composition is administered intramuscularly.

32. The composition of claim 1 wherein the composition is administered via central venous administration.

33. A method of treating a malignant, premalignant or benign tumor in a subject arising from or associated with the liver, comprising the steps of:
(a) providing a composition comprising tetra-O-methyl NDGA and a pharmaceutically acceptable carrier or excipient; and
(b) administering the composition to the subject;
wherein the composition is administered systemically by a route of administration other than by direct injection into or topical application onto the tumor, wherein the route of administration is selected from the group consisting of oral administration; inhalation administration; intra-arterial administration, with or without occlusion; intracranial administration; intraventricular administration; intravenous administration; intramuscular administration; implantation administration; and central venous administration.

34. The method of claim 33, wherein the composition is administered orally.

35. The method of claim 33, wherein the pharmaceutically acceptable carrier or excipient is an oil.

36. The method of claim 35, wherein the oil is castor oil or corn oil.

37. The method of claim 34, wherein the composition is present in an edible mix.

38. The method of claim 33, wherein the composition is administered daily.

39. The method of claim 38, wherein the composition is administered daily for 5 or more days to a week.

40. The method of claim 38, wherein the composition is administered daily for 5 or more days to 2 weeks.

41. The method of claim 38, wherein the composition is administered daily for 5 or more days to 3 weeks.

42. The method of claim 38, wherein the amount of tetra-O-methyl NDGA administered is at least 30 mg per dose.

43. The method of claim 38, wherein the amount of tetra-O-methyl NDGA administered is at least 90 mg per dose.

44. The method of claim 38, wherein the tetra-O-methyl NDGA is present in the composition at a concentration of 20 mg/mL.

45. The method of claim 33, wherein the pharmaceutically acceptable carrier or excipient comprises Cremaphor EL, ethanol and saline.

46. The composition of claim 33 wherein the composition is administered via inhalation.

47. The composition of claim 33 wherein the composition is administered via intra-arterial administration, with or without occlusion.

48. The composition of claim 33 wherein the composition is administered via intra-arterial administration, with or without occlusion.

49. The composition of claim 33 wherein the composition is administered via intracranial administration.

50. The composition of claim 33 wherein the composition is administered via intraventricular administration.

51. The composition of claim 33 wherein the composition is administered intravenously.

52. The composition of claim 33 wherein the composition is administered intramuscularly.

53. The composition of claim 33 wherein the composition is administered via central venous administration.

54. A method of treating a malignant, premalignant or benign tumor in a subject arising from or associated with the prostate, comprising the steps of:
  (a) providing a composition comprising tetra-O-methyl NDGA and a pharmaceutically acceptable carrier or excipient; and
  (b) administering the composition to the subject;
  wherein the composition is administered systemically by a route of administration other than by direct injection into or topical application onto the tumor, wherein the route of administration is selected from the group consisting of oral administration; inhalation administration; intra-arterial administration, with or without occlusion; intracranial administration; intraventricular administration; intravenous administration; intramuscular administration; implantation administration; and central venous administration.

55. The method of claim 54, wherein the composition is administered orally.

56. The method of claim 54, wherein the pharmaceutically acceptable carrier or excipient is an oil.

57. The method of claim 56, wherein the oil is castor oil or corn oil.

58. The method of claim 55, wherein the composition is present in an edible mix.

59. The method of claim 54, wherein the composition is administered daily.

60. The method of claim 57, wherein the composition is administered daily for 5 or more days to a week.

61. The method of claim 59, wherein the composition is administered daily for 5 or more days to 2 weeks.

62. The method of claim 59, wherein the composition is administered daily for 5 or more days to 3 weeks.

63. The method of claim 59, wherein the amount of tetra-O-methyl NDGA administered is at least 30 mg per dose.

64. The method of claim 59, wherein the amount of tetra-O-methyl NDGA administered is at least 90 mg per dose.

65. The method of claim 59, wherein the tetra-O-methyl NDGA is present in the composition at a concentration of 20 mg/mL.

66. The method of claim 54, wherein the pharmaceutically acceptable carrier or excipient comprises Cremaphor EL, ethanol and saline.

67. The composition of claim 54 wherein the composition is administered via inhalation.

68. The composition of claim 54 wherein the composition is administered via intra-arterial administration, with or without occlusion.

69. The composition of claim 54 wherein the composition is administered via intra-arterial administration, with or without occlusion.

70. The composition of claim 54 wherein the composition is administered via intracranial administration.

71. The composition of claim 54 wherein the composition is administered via intraventricular administration.

72. The composition of claim 54 wherein the composition is administered intravenously.

73. The composition of claim 54 wherein the composition is administered intramuscularly.

74. The composition of claim 54 wherein the composition is administered via central venous administration.

75. A method of treating a malignant, premalignant or benign tumor in a subject arising from or associated with the breast, comprising the steps of:
  (a) providing a composition comprising tetra-O-methyl NDGA and a pharmaceutically acceptable carrier or excipient; and
  (b) administering the composition to the subject;
  wherein the composition is administered systemically by a route of administration other than by direct injection into or topical application onto the tumor, wherein the route of administration is selected from the group consisting of oral administration; inhalation administration; intra-arterial administration, with or without occlusion; intracranial administration; intraventricular administration; intravenous administration; intramuscular administration; implantation administration; and central venous administration.

76. The method of claim 75, wherein the composition is administered orally.

77. The method of claim 75, wherein the pharmaceutically acceptable carrier or excipient is an oil.

78. The method of claim 77, wherein the oil is castor oil or corn oil.

79. The method of claim 76, wherein the composition is present in an edible mix.

80. The method of claim 75, wherein the composition is administered daily.

81. The method of claim 80, wherein the composition is administered daily for 5 or more days to a week.

82. The method of claim 80, wherein the composition is administered daily for 5 or more days to 2 weeks.

83. The method of claim 81, wherein the composition is administered daily for 5 or more days to 3 weeks.

84. The method of claim 75, wherein the amount of tetra-O-methyl NDGA administered is at least 30 mg per dose.

85. The method of claim 75, wherein the amount of tetra-O-methyl NDGA administered is at least 90 mg per dose.

86. The method of claim 75, wherein the tetra-O-methyl NDGA is present in the composition at a concentration of 20 mg/mL.

87. The method of claim 75, wherein the pharmaceutically acceptable carrier or excipient comprises Cremaphor EL, ethanol and saline.

88. The composition of claim 75 wherein the composition is administered via inhalation.

89. The composition of claim 75 wherein the composition is administered via intra-arterial administration, with or without occlusion.

90. The composition of claim 75 wherein the composition is administered via intra-arterial administration, with or without occlusion.

91. The composition of claim 75 wherein the composition is administered via intracranial administration.

92. The composition of claim 75 wherein the composition is administered via intraventricular administration.

93. The composition of claim 75 wherein the composition is administered intravenously.

94. The composition of claim 75 wherein the composition is administered intramuscularly.

95. The composition of claim 75 wherein the composition is administered via central venous administration.

* * * * *